US012370279B2

(12) United States Patent
Manka et al.

(10) Patent No.: US 12,370,279 B2
(45) Date of Patent: Jul. 29, 2025

(54) INTERNAL CLEANING FOR AUTONOMOUS VEHICLES

(71) Applicant: WAYMO LLC, Mountain View, CA (US)

(72) Inventors: Roman Manka, Brentwood, CA (US); Min Wang, Los Altos Hills, CA (US); Timothy Willis, San Jose, CA (US); Mark Alexander Shand, Palo Alto, CA (US)

(73) Assignee: Waymo LLC, Mountain View, CA (US)

( * ) Notice: Subject to any disclaimer, the term of this patent is extended or adjusted under 35 U.S.C. 154(b) by 338 days.

(21) Appl. No.: 17/202,476

(22) Filed: Mar. 16, 2021

(65) Prior Publication Data

US 2021/0346556 A1   Nov. 11, 2021

Related U.S. Application Data

(60) Provisional application No. 63/021,495, filed on May 7, 2020.

(51) Int. Cl.
*B60S 1/64* (2006.01)
*A61L 2/10* (2006.01)
*A61L 2/24* (2006.01)
*B60N 2/00* (2006.01)

(52) U.S. Cl.
CPC ..................... *A61L 2/24* (2013.01); *A61L 2/10* (2013.01); *B60N 2/0025* (2023.08); *B60S 1/64* (2013.01); *A61L 2202/11* (2013.01); *A61L 2202/14* (2013.01); *A61L 2202/17* (2013.01); *A61L 2202/25* (2013.01); *B60N 2210/18* (2023.08); *B60N 2210/40* (2023.08); *B60N 2230/20* (2023.08)

(58) Field of Classification Search
CPC .............. A61L 2/10; B60N 2/002; B60S 1/64
See application file for complete search history.

(56) References Cited

U.S. PATENT DOCUMENTS

| | | | |
|---|---|---|---|
| 8,859,994 B2 | 10/2014 | Deal | |
| 2015/0209458 A1* | 7/2015 | Kreitenberg | B64F 5/30 422/24 |
| 2017/0210353 A1* | 7/2017 | Stauffer | B60N 2/58 |

(Continued)

FOREIGN PATENT DOCUMENTS

WO    2017034487 A2    3/2017

OTHER PUBLICATIONS

Adrienne Murray, Coronoavirus: Robots use light beams to zap hospital viruses., https://www.bbc.com/news/business-51914722, retrieved from internet on Mar. 30, 2020, pp. 1-6.

(Continued)

*Primary Examiner* — Kevin Joyner
(74) *Attorney, Agent, or Firm* — Botos Churchill IP Law

(57) ABSTRACT

Aspects of the disclosure relate cleaning systems for cleaning cabin air and interior surfaces of a vehicle. For instance, a cleaning system may include a surface cleaning device including a UVC light source. In addition, a request for confirmation that the vehicle may not be occupied may be sent to a remote computing device. In response to the request, a signal indicating whether or not the vehicle is occupied may be received. The surface cleaning device may then be activated based on the signal.

19 Claims, 16 Drawing Sheets

(56) References Cited

U.S. PATENT DOCUMENTS

| | | | |
|---|---|---|---|
| 2018/0079322 A1* | 3/2018 | Tanriover | B60R 21/01512 |
| 2019/0091738 A1* | 3/2019 | Chen | B60H 1/00742 |
| 2019/0176768 A1 | 6/2019 | Diaz Garcia et al. | |
| 2019/0370575 A1* | 12/2019 | Nandakumar | G05D 1/0088 |
| 2020/0061223 A1 | 2/2020 | Hallack | |

OTHER PUBLICATIONS

Brian Cooley, Clean your car with the right stuff to fight viruses and germs, Roadshow, Apr. 17, 2020, pp. 1-6, CNET.

Combating coronavirus—Keeping your car clean and germ-free, https://www.thenewsmarket.com/news/combating-coronavirus---keeping-your-car-clean-and-germ-free/s/18e50712-6419-47b9-b25c-5182f66b8cd4, retrieved from internet Mar. 30, 2020, pp. 1-2.

Disinfecting EMS Vehicles with Ultraviolet Light, https://www.frazerbilt.com/blog-ambulance-disinfection-system/, retrieved from internet Mar. 30, 2020, pgs.

GHSP Announces Debut of UV-C Techno grenlite™ at CES, https://www.ghsp.com/news/ghsp-announces-debut-of-uv-c-technology-brand-greenlite-at-ces, retrieved from internet Mar. 30, 2020, pp. 1-3.

Jake Holmes, Jaguar Land Rover could use ultraviolet light to kills germs in your car, Road Show, Mar. 27, 2019, pp. 1-3, CNET.

Lynn Walford, Combating Coronavirus and Other Bugs—Keeping Your Car Clean, Odourless & Disinfected, https://www.autofutures.tv/2020/02/24/how-to-keep-your-car-virus-free/, retrieved from internet Mar. 30, 2020, pp. 1-5.

Soon your car might help keep you healthy., The Week, Jun. 1, 2019, pp. 1-3. The Week Publications Inc.

Billington, James, "Smart and self-cleaning: Yanfeng unveils autonomous cabin of the future", https://www.autonomousvehicleinternational.com/news/concept-vehicles/smart-and-self-cleaning-yanfeng-unveils-autonomous-cabin-of-the-future.html, retrieved from internet Mar. 30, 2020, pp. 1-2.

* cited by examiner

INTERNAL CLEANING FOR AUTONOMOUS VEHICLES

CROSS REFERENCE TO RELATED APPLICATION

This application claims the benefit of the filing date of U.S. Provisional Patent Application No. 63/021,495 filed May 7, 2020, the disclosure of which is hereby incorporated herein by reference.

BACKGROUND

With the possibility of pandemics and spreading diseases it is becoming increasingly important to maintain a high level of cleanliness of the air and interior surfaces inside of vehicles which provide transportation services in order to minimize opportunities to spread viruses and diseases among passengers. However, many options for cleaning may be suboptimal; they may not leave the vehicle sufficiently clean and may not be appropriate when the vehicle is occupied (as with a typical taxi which includes a human driver). At the same time, autonomous vehicles, such as vehicles that do not require a human driver, can be used to aid in the transport of passengers or items from one location to another. Such vehicles may operate in a fully autonomous mode where passengers may provide some initial input, such as a pickup or destination location, and the vehicle maneuvers itself to that location.

BRIEF SUMMARY

One aspect of the disclosure provides a method for activating surface cleaning to clean interior surfaces of an autonomous vehicle. The method includes sending, by one or more processors of the vehicle to a remote computing device, a request for confirmation that the vehicle is not occupied; in response to the request, receiving, by the one or more processors a signal indicating whether or not the vehicle is occupied; and activating, by the one or more processors, a surface cleaning device based on the signal.

In one example, the surface cleaning device includes an ultraviolet C (UVC) light source in order to clean the interior surfaces. In another example, the sending further includes sending feedback from one or more sensors mounted within the vehicle. In this example, the surface cleaning device is incorporated into a cleaning system including the one or more sensors. In another example, the signal indicates that a human operator has determined that the vehicle is not occupied. In another example, the method also includes, determining, by the one or more processors, based on feedback from one or more sensors, whether the vehicle is occupied, and wherein the sending is after the determining. In this example, the sending further includes sending the determination of whether the vehicle is occupied to the remote computing device. In addition, the method also includes determining a confidence for the determination of whether the vehicle is occupied and determining whether the confidence meets a threshold value, and wherein the sending is based on the determining whether the confidence meets the threshold value. In another example, the sending is performed between rides for the vehicle, wherein each of the rides includes the vehicle transporting passengers or cargo. In this example, the activating is performed while the vehicle is moving between the rides. Alternatively, the activating is performed while the vehicle is stationary between the rides. In another example, the sending is in response to receiving dispatching instructions to pick up a passenger. In this example, the dispatching instructions include a request for the vehicle to activate the surface cleaning device. In another example, the activating includes sending a signal to a cleaning system to cause the surface cleaning device to move along one or more rails within the vehicle. In another example, the method also includes, after activating the surface cleaning device and while the surface cleaning device is activated, determining, by the one or more processors, based on feedback from one or more sensors, whether the vehicle is occupied. In this example, when the vehicle is determined to be occupied, deactivating the surface cleaning device. In another example, the method also includes, prior to activating the surface cleaning device, confirming, by the one or more processors, that windows of the vehicle are closed. In another example, the method also includes, prior to the activating, using information from a perception system of the vehicle including one or more sensors to check an area around the vehicle for people.

Another aspect of the disclosure provides a system for activating surface cleaning to clean interior surfaces of an autonomous vehicle. The system includes a surface cleaning device including a UVC light source and one or more processors. The one or more processors are further configured to send, to a remote computing device, a request for confirmation that the vehicle is not occupied; in response to the request, receive a signal indicating whether or not the vehicle is occupied; and activate the surface cleaning device based on the signal.

In one example, the system also includes the vehicle.

DETAILED DESCRIPTION

Overview

Figure 1:
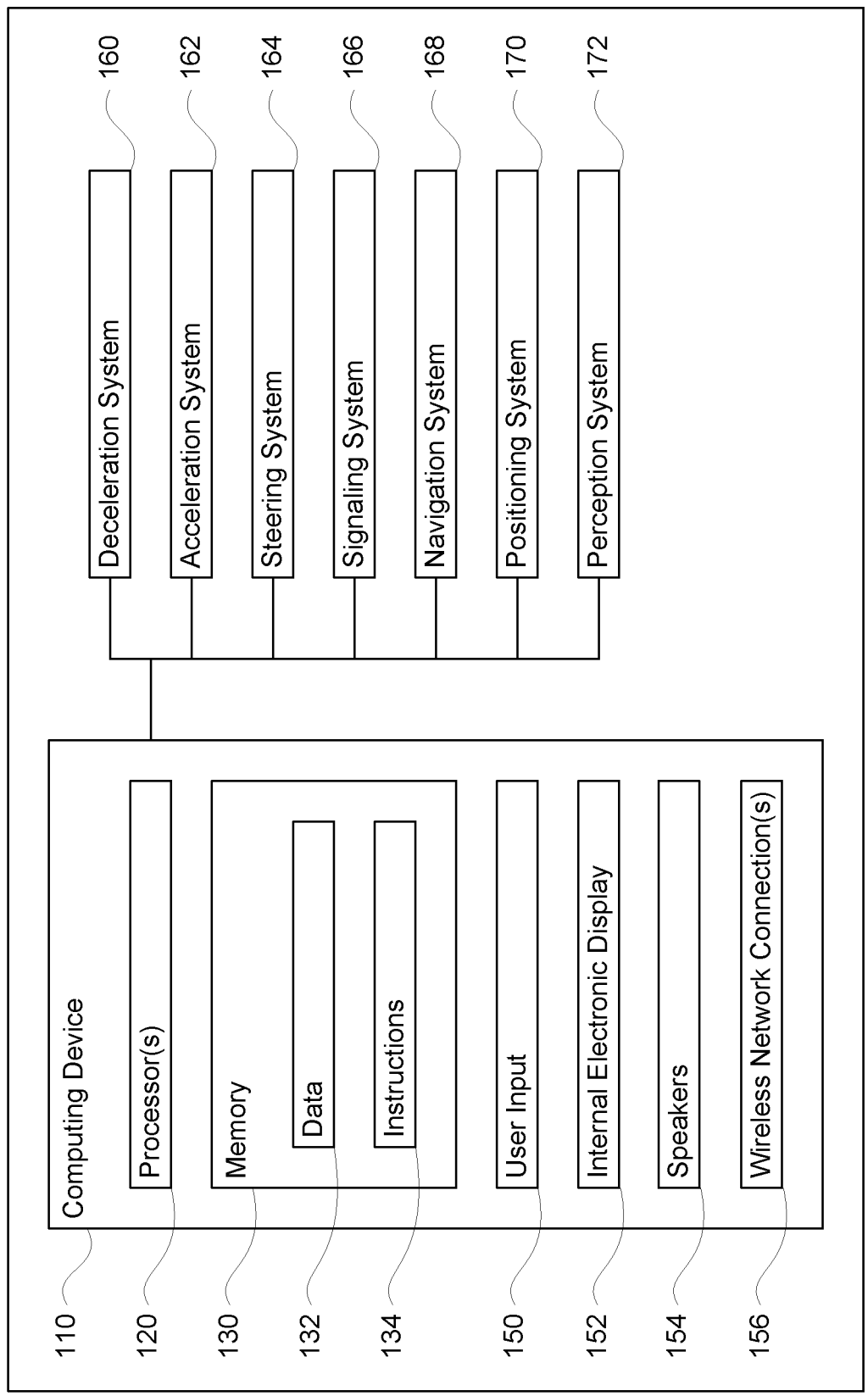
FIG. 1 is a functional diagram of an example vehicle in accordance with an exemplary embodiment.

As noted above, with the possibility of pandemics and spreading diseases it is becoming increasingly important to maintain a high level of cleanliness of the air and interior surfaces inside of vehicles which provide transportation services in order to minimize opportunities to spread viruses and diseases among passengers. However, many options for cleaning may be suboptimal; they may not leave the vehicle sufficiently clean and may not be appropriate when the vehicle is occupied (as with a typical taxi which includes a human driver). However, with the case of an autonomous vehicle, between trips or when there are trips without any passengers (such as those that are completely empty or are used to transport only cargo), the vehicle is unoccupied by any people. This may enable such vehicles to be subjected to rigorous cleaning.

An example cleaning device for an autonomous vehicle may be arranged on a headliner of the vehicle. The cleaning device may include various features that may be used to clean air inside the cabin of the vehicle as well as surfaces inside of the cabin of the vehicle. For instance, the cleaning system may include one or more air cleaning devices for cleaning the air within the cabin and one or more surface cleaning devices for cleaning surfaces of the vehicle. The air and surface cleaning devices discussed herein may employ ultraviolet C (UVC) light rays generated by UVC light sources to clean air and surfaces. The cleaning device may also include sensors which can be used to detect whether the vehicle is occupied by passengers or other occupants.

While such light rays may be an effective way to kill viruses, bacteria and fungi, humans typically experience very little exposure. Most UVC light rays from the sun and other light sources do not penetrate the upper atmosphere. However, UVC light rays may cause damage to a person's skin or eyes, and may even cause diseases such as cancer or cataracts. In this regard, it may be critically important to ensure that the vehicle is unoccupied by any passengers before utilizing the aforementioned surface cleaning devices. However, as noted above, the air cleaning devices may actually operate continuously, because if such devices utilize UVC light rays, they may be internal to the cleaning devices, and therefore may not raise concerns over exposure to passengers of the vehicle.

In order to avoid exposure of UVC light rays to passengers, the computing devices of the vehicle may first attempt to confirm that the vehicle is unoccupied. As such, the surface cleaning may be scheduled to be activated between passenger rides or during rides which do not include any passengers, such as those that transport only cargo. In this regard, the surface cleaning may be utilized fairly often without impacting availability of the service.

For instance, the vehicle's computing devices may send a request for confirmation that the vehicle is not occupied or currently empty. For instance, this may involve sending feedback or signals from the one or more sensors of the vehicle and/or the cleaning device to a remote computing device via a network. A human operator may review the feedback or signals at the remote computing devices in order to determine whether the vehicle is occupied by passengers or other persons. The human operator may identify whether or not the vehicle is occupied, and the remote computing device may send a signal identifying whether or not the vehicle is occupied back to the computing devices of the vehicle via the network.

The computing device of the vehicle may receive the signal identifying whether or not the vehicle is occupied may be received. Based on the signal, the computing devices of the vehicle may determine whether to activate the surface cleaning devices, and the surface cleaning devices may be activated based on the received signal. In some instances, the computing devices of the vehicle may also determine whether the vehicle is occupied using the aforementioned feedback and signals. This may be used as an initial step to determine whether to activate the surface cleaning devices, as a signal to determine whether to request confirmation from a human operator, as an additional signal for a human operator to consider, or as a check on the determination of a human operator.

The features described herein may provide a useful and reliable way to clean the interior of a vehicle. As noted above, in addition to cleaning the air of the cabin of a vehicle, the cleaning systems and devices described herein may provide a safe and reliable way to clean surfaces of a vehicle. In addition, by utilizing UVC light rays, the cleaning may attempt to sanitize or disinfect surfaces of the vehicle by killing viruses, bacteria and fungi. UVC light rays may be utilized more often with autonomous vehicles which do not require a driver as compared to typical taxies with a human driver because there may be more opportunities to clean the vehicle (i.e. times when there are no occupants within the vehicle) between passenger rides or during rides without any passengers (or driver) to transport cargo. In addition, by utilizing a human operator to review feedback and signals from various sensors, rather than relying only on the computing devices of the vehicle, a human operator is able to check and confirm remotely that the vehicle is not occupied before activating the surface cleaning devices, thus greatly decreasing the likelihood of accidental exposure of passengers or other persons to UVC light rays. In addition, in some cases, the human operator may be better able to identify a partially occluded object as a person than the computing devices of the vehicle, thus improving the safety of the system. Moreover, by utilizing the surface cleaning devices between rides, the cleaning need not impact the availability of a transportation service.

Example Systems

As shown in FIG. 1, a vehicle 100 in accordance with one aspect of the disclosure includes various components. While certain aspects of the disclosure are particularly useful in connection with specific types of vehicles, the vehicle may be any type of vehicle including, but not limited to, cars, trucks, motorcycles, buses, recreational vehicles, etc. The vehicle may have one or more computing devices, such as computing device 110 containing one or more processors 120, memory 130 and other components typically present in general purpose computing devices.

The memory 130 stores information accessible by the one or more processors 120, including instructions 134 and data 132 that may be executed or otherwise used by the processor 120. The memory 130 may be of any type capable of storing information accessible by the processor, including a computing device-readable medium, or other medium that stores data that may be read with the aid of an electronic device, such as a hard-drive, memory card, ROM, RAM, DVD or other optical disks, as well as other write-capable and read-only memories. Systems and methods may include different combinations of the foregoing, whereby different portions of the instructions and data are stored on different types of media.

The instructions 134 may be any set of instructions to be executed directly (such as machine code) or indirectly (such as scripts) by the processor. For example, the instructions may be stored as computing device code on the computing device-readable medium. In that regard, the terms "instructions" and "programs" may be used interchangeably herein. The instructions may be stored in object code format for direct processing by the processor, or in any other computing device language including scripts or collections of independent source code modules that are interpreted on demand or compiled in advance. Functions, methods and routines of the instructions are explained in more detail below.

The data 132 may be retrieved, stored or modified by processor 120 in accordance with the instructions 134. For instance, although the claimed subject matter is not limited by any particular data structure, the data may be stored in computing device registers, in a relational database as a table having a plurality of different fields and records, XML documents or flat files. The data may also be formatted in any computing device-readable format.

The one or more processor 120 may be any conventional processors, such as commercially available CPUs. Alternatively, the one or more processors may be a dedicated device such as an ASIC or other hardware-based processor. Although FIG. 1 functionally illustrates the processor, memory, and other elements of computing device 110 as being within the same block, it will be understood by those of ordinary skill in the art that the processor, computing device, or memory may actually include multiple processors, computing devices, or memories that may or may not be stored within the same physical housing. For example, memory may be a hard drive or other storage media located in a housing different from that of computing device 110. Accordingly, references to a processor or computing device will be understood to include references to a collection of processors or computing devices or memories that may or may not operate in parallel.

Computing device 110 may all of the components normally used in connection with a computing device such as the processor and memory described above as well as a user input 150 (e.g., a mouse, keyboard, touch screen and/or microphone) and various electronic displays (e.g., a monitor having a screen or any other electrical device that is operable to display information). In this example, the vehicle includes an internal electronic display 152 as well as one or more speakers 154 to provide information or audio-visual experiences. In this regard, internal electronic display 152 may be located within a cabin of vehicle 100 and may be used by computing device 110 to provide information to passengers within the vehicle 100.

Computing device 110 may also include one or more wireless network connections 156 to facilitate communication with other computing devices, such as the client computing devices and server computing devices described in detail below. The wireless network connections may include short range communication protocols such as Bluetooth, Bluetooth low energy (LE), cellular connections, as well as various configurations and protocols including the Internet, World Wide Web, intranets, virtual private networks, wide area networks, local networks, private networks using communication protocols proprietary to one or more companies, Ethernet, WiFi and HTTP, and various combinations of the foregoing.

In one example, computing device 110 may be an autonomous driving computing system incorporated into vehicle 100. The autonomous driving computing system may be capable of communicating with various components of the vehicle. For example, returning to FIG. 1, computing device 110 may be in communication with various systems of vehicle 100, such as deceleration system 160, acceleration system 162, steering system 164, signaling system 166, navigation system 168, positioning system 170, and perception system 172 in order to control the movement, speed, etc. of vehicle 100 in accordance with the instructions 134 of memory 130. Again, although these systems are shown as external to computing device 110, in actuality, these systems may also be incorporated into computing device 110, again as an autonomous driving computing system for controlling vehicle 100.

As an example, computing device 110 may interact with deceleration system 160 and acceleration system 162 in order to control the speed of the vehicle. Similarly, steering system 164 may be used by computing devices 110 in order to control the direction of vehicle 100. For example, if vehicle 100 is configured for use on a road, such as a car or truck, the steering system may include components to control the angle of wheels to turn the vehicle. Signaling system 166 may be used by computing device 110 in order to signal the vehicle's intent to other drivers or vehicles, for example, by lighting turn signals or brake lights when needed.

Navigation system 168 may be used by computing device 110 in order to determine and follow a route to a location. In this regard, the navigation system 168 and/or data 132 may store detailed map information, e.g., highly detailed maps identifying the shape and elevation of roadways, lane lines, intersections, crosswalks, speed limits, traffic signals, buildings, signs, real time traffic information, pull over spots vegetation, or other such objects and information. As discussed further below, these pull over spots may be "hand" selected or identified areas where at which the vehicle is lawfully able to stop and park for some period of time such as shoulder areas, parking spots, parking lots, emergency pull over spots, etc.

Positioning system 170 may be used by computing device 110 in order to determine the vehicle's relative or absolute position on a map or on the earth. For example, the position system 170 may include a GPS receiver to determine the device's latitude, longitude and/or altitude position. Other location systems such as laser-based localization systems, inertial-aided GPS, or camera-based localization may also be used to identify the location of the vehicle. The location of the vehicle may include an absolute geographical location, such as latitude, longitude, and altitude as well as relative location information, such as location relative to other cars immediately around it which can often be determined with less noise that absolute geographical location.

The positioning system 170 may also include other devices in communication with computing device 110, such as an accelerometer, gyroscope or another direction/speed detection device to determine the direction and speed of the vehicle or changes thereto. By way of example only, an acceleration device may determine its pitch, yaw or roll (or changes thereto) relative to the direction of gravity or a plane perpendicular thereto. The device may also track increases or decreases in speed and the direction of such changes. The device's provision of location and orientation data as set forth herein may be provided automatically to the computing device 110, other computing devices and combinations of the foregoing.

The perception system 172 also includes one or more components for detecting objects external to the vehicle such as other vehicles, obstacles in the roadway, traffic signals, signs, trees, etc. For example, the perception system 172 may include lasers, sonar, radar, cameras and/or any other detection devices that record data which may be processed by computing device 110. In the case where the vehicle is a small passenger vehicle such as a car, the car may include a laser or other sensors mounted on the roof or other convenient location.

The computing device 110 may control the direction and speed of the vehicle by controlling various components. By way of example, computing device 110 may navigate the vehicle to a destination location completely autonomously using data from the detailed map information and navigation system 168. Computing device 110 may use the positioning system 170 to determine the vehicle's location and perception system 172 to detect and respond to objects when needed to reach the location safely. In order to do so, computing device 110 may cause the vehicle to accelerate (e.g., by increasing fuel or other energy provided to the engine by acceleration system 162), decelerate (e.g., by decreasing the fuel supplied to the engine, changing gears, and/or by applying brakes by deceleration system 160), change direction (e.g., by turning the front or rear wheels of vehicle 100 by steering system 164), and signal such changes (e.g., by lighting turn signals of signaling system 166). Thus, the acceleration system 162 and deceleration system 160 may be a part of a drivetrain that includes various components between an engine of the vehicle and the wheels of the vehicle. Again, by controlling these systems, computing device 110 may also control the drivetrain of the vehicle in order to maneuver the vehicle autonomously.

Figure 2:
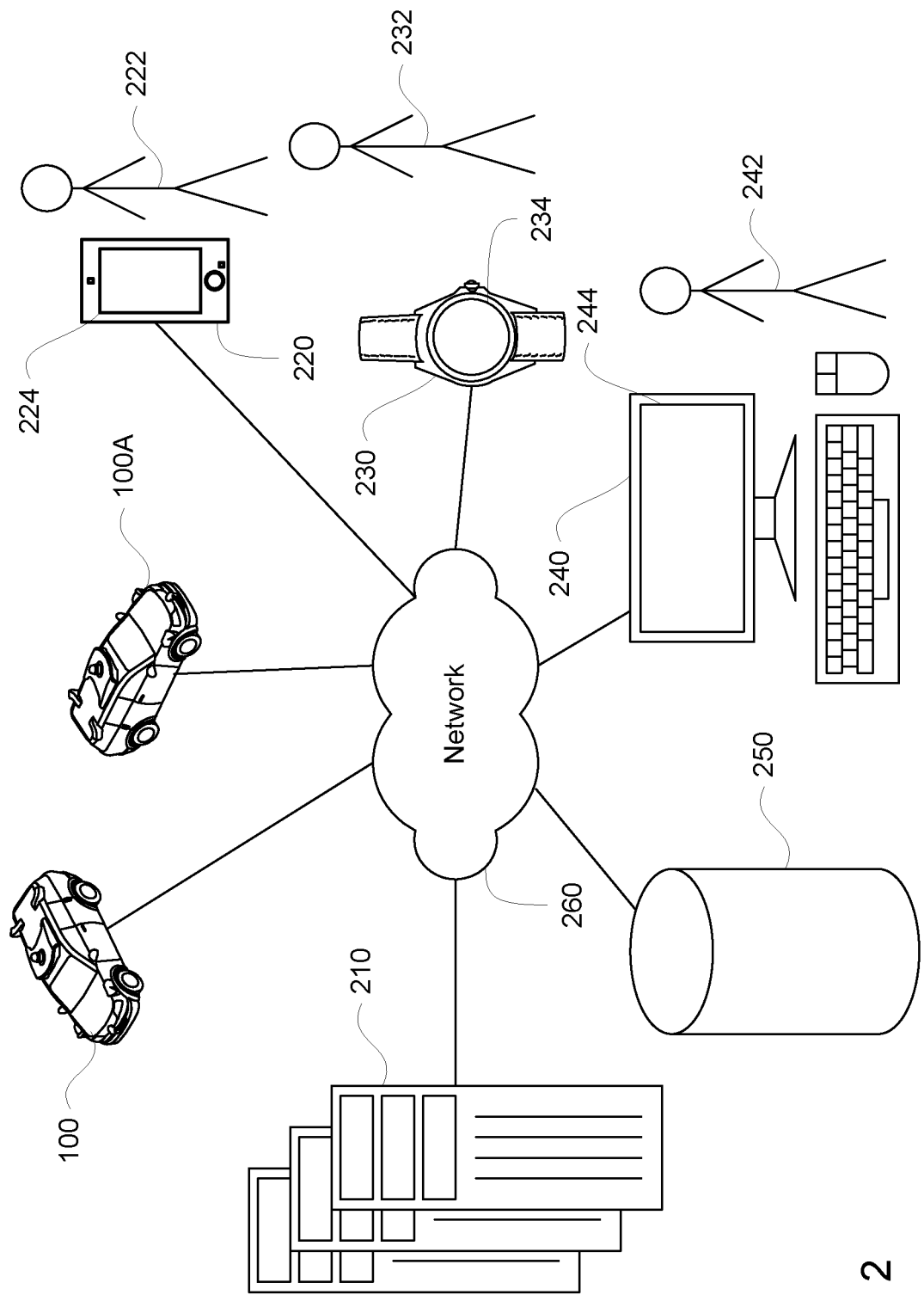
FIG. 2 is a functional diagram of an example system in accordance with aspects of the disclosure.
Figure 3:
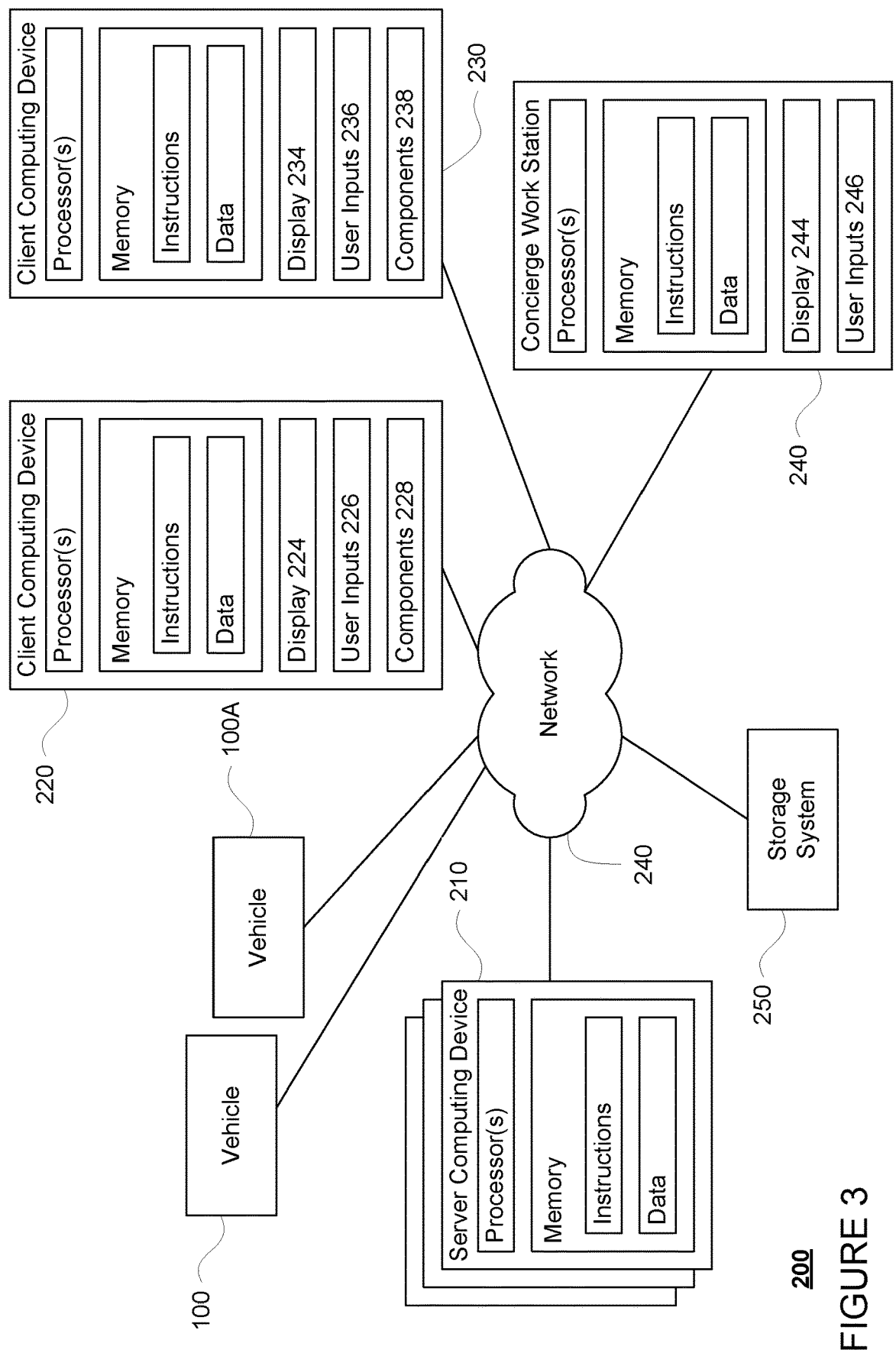
FIG. 3 is a pictorial diagram of the system of FIG. 2 in accordance with aspects of the disclosure.

Computing device 110 of vehicle 100 may also receive or transfer information to and from other computing devices. FIGS. 2 and 3 are pictorial and functional diagrams, respectively, of an example system 200 that includes a plurality of computing devices 210, 220, 230, 240 and a storage system 250 connected via a network 260. System 200 also includes vehicle 100, and vehicle 100A which may be configured similarly to vehicle 100. Although only a few vehicles and computing devices are depicted for simplicity, a typical system may include significantly more.

As shown in FIG. 3, each of computing devices 210, 220, 230, 240 may include one or more processors, memory, data and instructions. Such processors, memories, data and instructions may be configured similarly to one or more processors 120, memory 130, data 132, and instructions 134 of computing device 110.

The network 260, and intervening nodes, may include various configurations and protocols including short range communication protocols such as Bluetooth, Bluetooth LE, the Internet, World Wide Web, intranets, virtual private networks, wide area networks, local networks, private networks using communication protocols proprietary to one or more companies, Ethernet, WiFi and HTTP, and various combinations of the foregoing. Such communication may be facilitated by any device capable of transmitting and receiving data to and from other computing devices, such as modems and wireless interfaces.

In one example, one or more computing devices 110 may include a server having a plurality of computing devices, e.g., a load balanced server farm, that exchange information with different nodes of a network for the purpose of receiving, processing and transmitting the data to and from other computing devices. For instance, one or more computing devices 210 may include one or more server computing devices that are capable of communicating with computing device 110 of vehicle 100 or a similar computing device of vehicle 100A as well as computing devices 220, 230, 240 via the network 260. For example, vehicles 100 and 100A may be a part of a fleet of vehicles that can be dispatched by server computing devices to various locations. In this regard, the vehicles of the fleet may periodically send the server computing devices location information provided by the vehicle's respective positioning systems and the one or more server computing devices may track the locations of the vehicles.

In addition, server computing devices 210 may use network 260 to transmit and present information to a user, such as user 222, 232, 242 on a display, such as displays 224, 234, 244 of computing devices 220, 230, 240. In this regard, computing devices 220, 230, 240 may be considered client computing devices.

As shown in FIG. 3, each client computing device 220, 230, 240 may be a personal computing device intended for use by a user 222, 232, 242, and have all of the components normally used in connection with a personal computing device including a one or more processors (e.g., a central processing unit (CPU)), memory (e.g., RAM and internal hard drives) storing data and instructions, a display such as displays 224, 234, 244 (e.g., a monitor having a screen, a touch-screen, a projector, a television, or other device that is operable to display information), and user input devices 226, 236, 246 (e.g., a mouse, keyboard, touchscreen or microphone). The client computing devices may also include a camera for recording video streams, speakers, a network interface device, and all of the components used for connecting these elements to one another.

In addition, the client computing devices 220, 230 may also include components 228, 238 for determining the position and orientation of client computing devices. For example, these components may include a GPS receiver to determine the device's latitude, longitude and/or altitude as well as an accelerometer, gyroscope or another direction/speed detection device as described above with regard to positioning system 170 of vehicle 100.

Although the client computing devices 220, 230, and 240 may each comprise a full-sized personal computing device, they may alternatively comprise mobile computing devices capable of wirelessly exchanging data with a server over a network such as the Internet. By way of example only, client computing device 220 may be a mobile phone or a device such as a wireless-enabled PDA, a tablet PC, a wearable computing device or system, or a netbook that is capable of obtaining information via the Internet or other networks. In another example, client computing device 230 may be a wearable computing system, shown as a wrist watch in FIG. 2. As an example the user may input information using a small keyboard, a keypad, microphone, using visual signals with a camera, or a touch screen.

In some examples, client computing device 240 may be a concierge work station used by an administrator to provide concierge services to users such as users 222 and 232. For example, a user 242 as a human operator may be a "concierge", and may thus use the concierge work station 240 to communicate via a telephone call or audio connection with users through their respective client computing devices or vehicles 100 or 100A in order to facilitate the safe operation of vehicles 100 and 100A and the safety of passengers and other occupants as described in further detail below. Although only a single concierge work station 240 is shown in FIGS. 2 and 3, any number of such work stations may be included in a typical system.

Storage system 250 may store various types of information as described in more detail below. This information may be retrieved or otherwise accessed by a server computing device, such as one or more server computing devices 210 and concierge work station 240, in order to perform some or all of the features described herein.

As with memory 130, storage system 250 can be of any type of computerized storage capable of storing information accessible by the server computing devices 210, such as a hard-drive, memory card, ROM, RAM, DVD, CD-ROM, write-capable, and read-only memories. In addition, storage system 250 may include a distributed storage system where data is stored on a plurality of different storage devices which may be physically located at the same or different geographic locations. Storage system 250 may be connected to the computing devices via the network 260 as shown in FIG. 2 and/or may be directly connected to or incorporated into any of the computing devices 110, 210, 220, 230, 240, etc.

Figure 4:
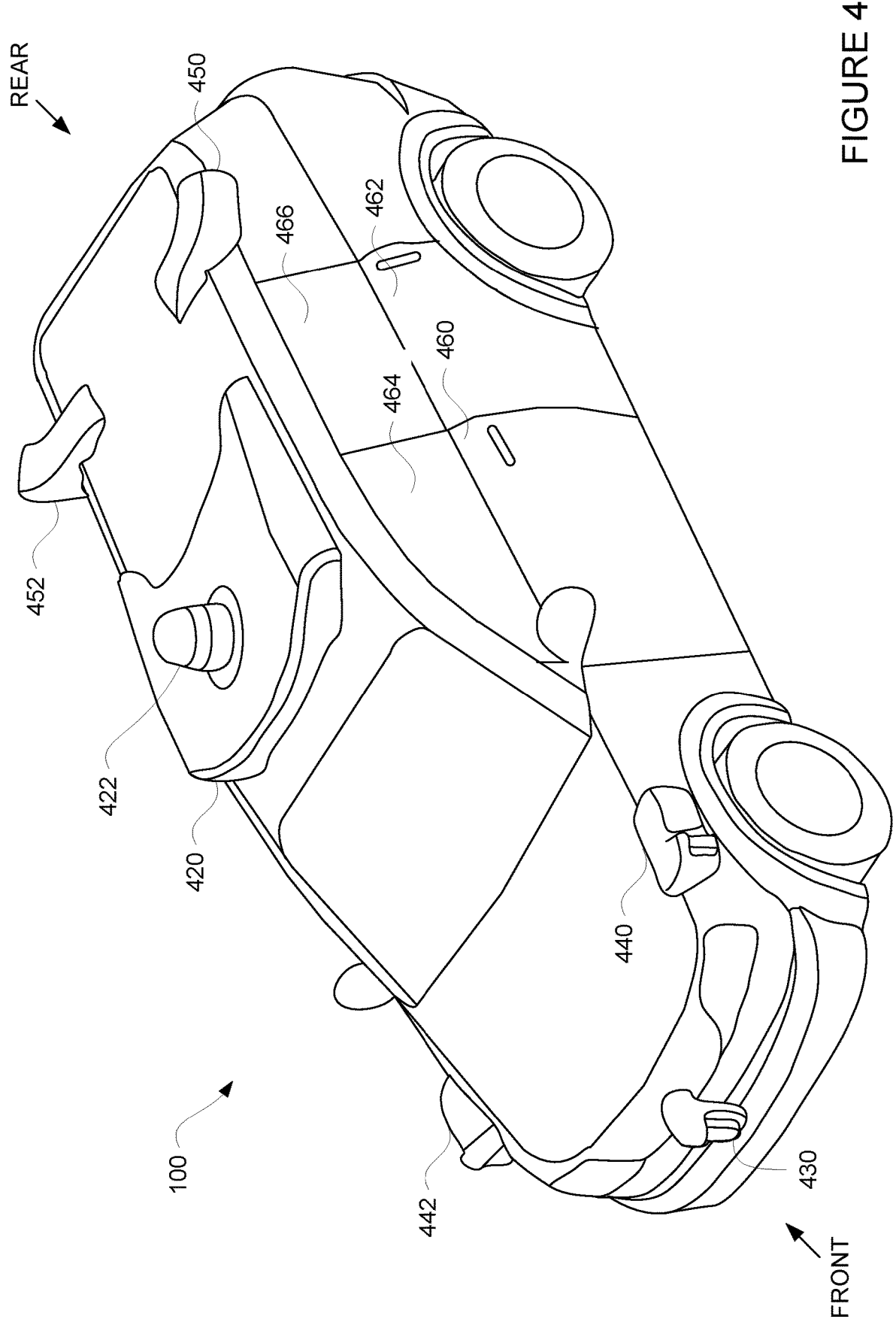
FIG. 4 is an example external view of a vehicle in accordance with aspects of the disclosure.

Vehicle 100 also includes sensors of the perception system 172. FIG. 4 is an example configuration for vehicle 100. In this example, roof-top housing 420 and dome housing 422 may include a lidar sensor as well as various cameras and radar units. In addition, housing 430 located at the front end of vehicle 100 and housings 440, 442 on the driver's and passenger's sides of the vehicle may each store a lidar sensor. For example, housing 440 is located in front of driver door 460. In this regard, the vehicle includes driver door 460, passenger door 462 as well as windows 464, 466. Vehicle 100 also includes housings 450, 452 for radar units and/or cameras also located on the roof of vehicle 100. Additional radar units and cameras (not shown) may be located at the front and rear ends of vehicle 100 and/or on other positions along the roof or roof-top housing 420. Each of these radar, camera, and laser sensors or devices may be associated with processing components which process data from these devices as part of the perception system 172 and provide sensor data to the computing device 110.

Figure 5:
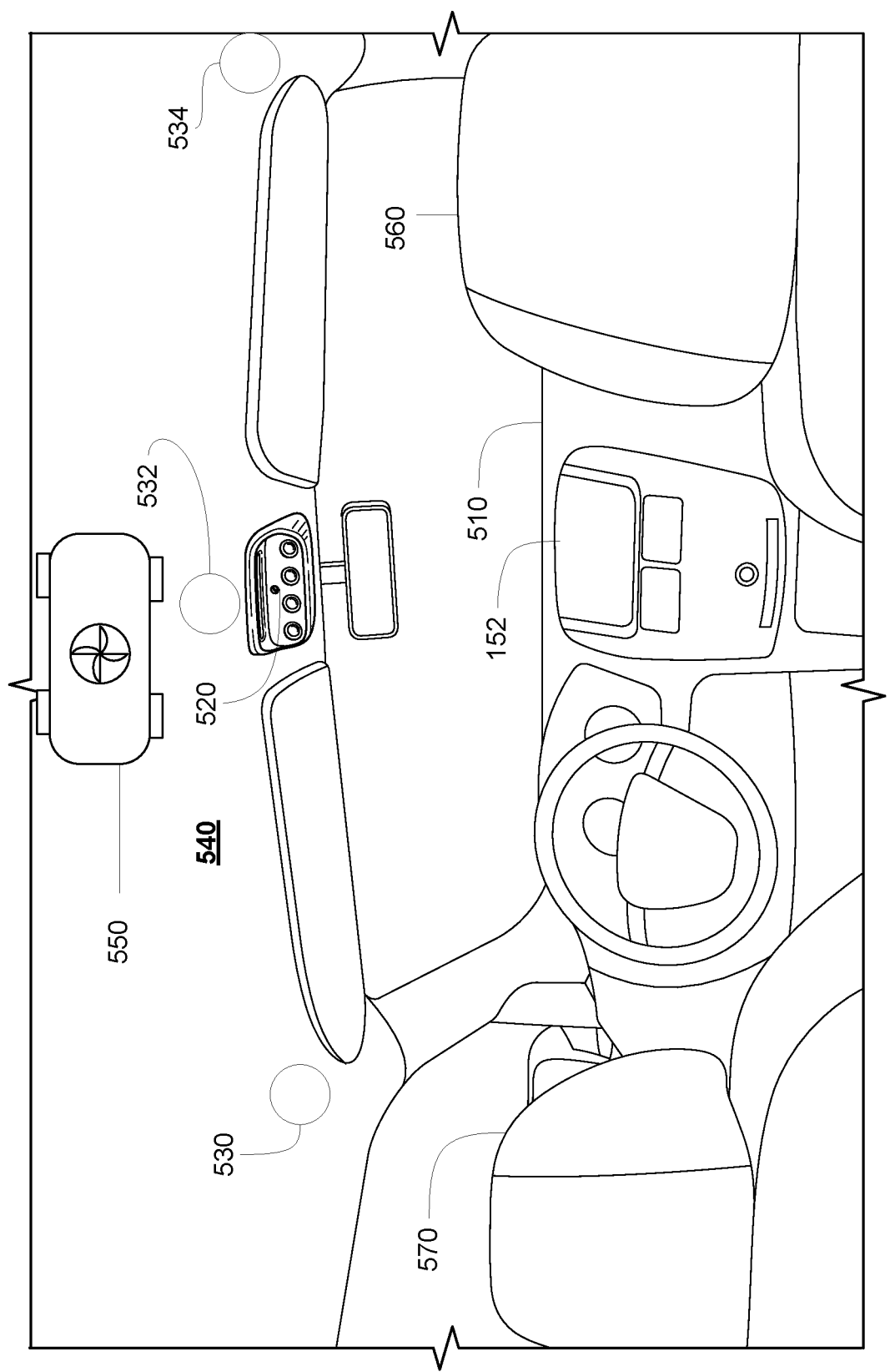
FIG. 5 is an example internal view of a cabin of a vehicle in accordance with aspects of the disclosure.
Figure 6:
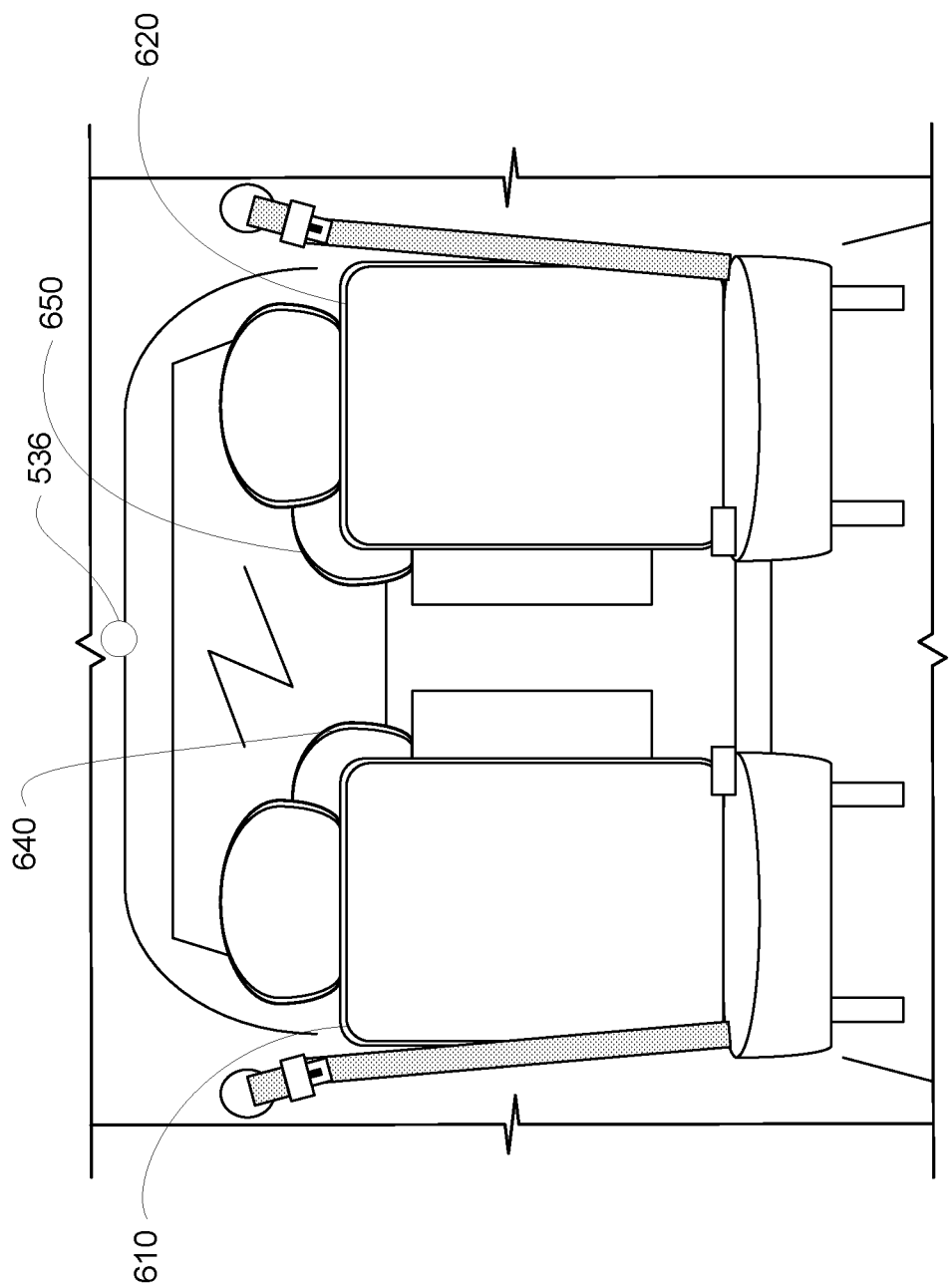
FIG. 6 is an example internal view of a cabin of a vehicle in accordance with aspects of the disclosure.

FIG. 5 is an example internal view of a cabin of a vehicle 100, for instance in the example configuration of FIG. 4 looking towards the front of the vehicle 100. In this view, seats 560, 570 of a first row of seating of vehicle 100 are visible. FIG. 6 is an example internal view of a cabin of a vehicle 100, for instance in the example configuration of FIG. 4 looking towards the rear of the vehicle 100. In this view, seats 610, 620 of a second row of seating of vehicle 100 as well as part of seats 640, 650 of a third row of seating of vehicle 100 are visible.

For instance, in the view of FIG. 5, a dashboard area 510 which includes the internal electronic display 152 is visible. Although vehicle 100 includes a steering wheel, gas (acceleration) pedal, or brake (deceleration) pedal which would allow for a semi-autonomous or manual driving mode where a passenger would directly control the steering, acceleration and/or deceleration of the vehicle via the drivetrain, these inputs are not necessary for the autonomous driving mode. Rather, as described in further detail below, user input is limited to a microphone of the user input 150 (not shown), buttons or other features of a console 520, and wireless network connections 156. In this regard, internal electronic display 152 merely provides information to the passenger and need not include a touch screen or other interface for user input. In other embodiments, the internal electronic display 152 may include a touch screen or other user input device for entering information by a passenger such as a destination, etc.

In order to determine whether a vehicle is occupied, one or more sensors may be mounted within the vehicle. For instance, a sensor may be mounted in the front of the vehicle in the left, middle or right side of the headliner and oriented towards the rear interior of the vehicle in order to view locations where passengers could be present. For instance, FIG. 5 depicts sensors 530, 532, and 534 mounted within the headliner area 540 of vehicle 100. Other additional sensors may also be placed throughout the interior of the vehicle. For instance, referring to FIG. 6 an additional sensor 536 may be mounted between a middle row of seats (including seats 610 and 620) to get a useful view of the rear seats 640, 650. These sensors may include any type of sensors which can be used to determine whether the vehicle 100 is occupied. For example, the sensors 530, 532, 534 may include infrared sensors (to detect heat), passive infrared sensors (which can detect motion), carbon dioxide level detectors (which can be used to detect slight changes in CO2 over time which may indicate that the vehicle is occupied), inertial measurement units (IMUs) (which can be used to detect instances of passenger/luggage ingress to, egress from, the vehicle), load sensors on vehicle wheels/suspension (which can be used to detect loading of the vehicle for example, by comparing current weight to expected unladen vehicle weight—which may also include accounting for and fuel tank or cleaning fluids contents—against actual vehicle weight to detect presence of unaccounted mass in vehicle which can indicate occupancy, typical visible light still or video cameras, event based cameras, stereo cameras (which may provide from three-dimensional information), time of flight cameras and/or an infrared cameras that can capture images of the vehicle in very low light conditions, such as at night time, during inclement weather, or when the vehicle is in a tunnel or parking garage. In addition or alternatively, the aforementioned sensors may be placed in order to view areas underneath the seats and into any cargo areas.

Figure 7:
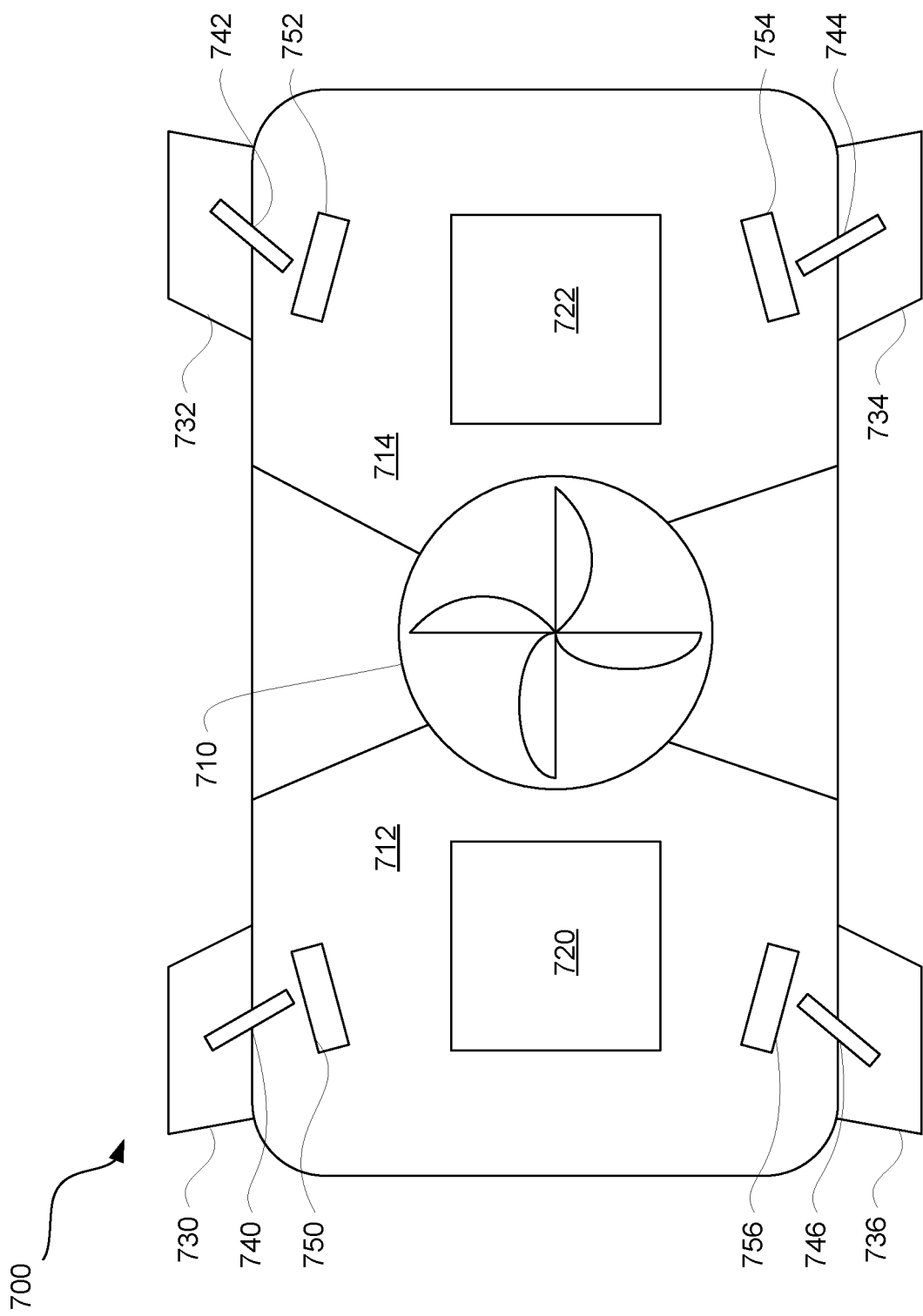
FIG. 7 is an example bottom-up cross-sectional view of a cleaning device in accordance with aspects of the disclosure.
Figure 8:
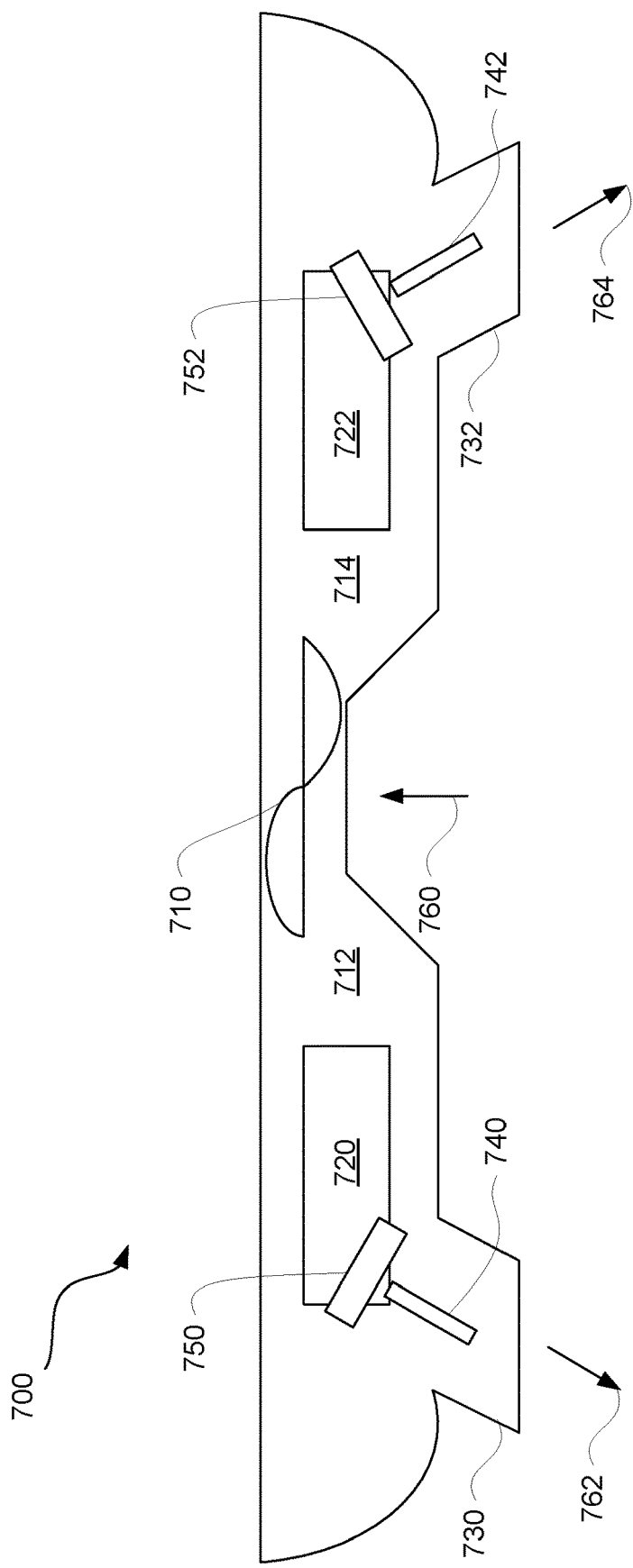
FIG. 8 is an example side cross-sectional view of a cleaning device in accordance with aspects of the disclosure.

Returning to 5, headliner area 540 also includes a cleaning system 550. Cleaning system may include various features that may be used to clean air inside the cabin of the vehicle 100 as well as surfaces inside of the cabin of the vehicle. FIGS. 7 and 8 provide detail view of an example configuration of a cleaning system 700 which may be the same as or similar to cleaning system 550. FIG. 7 provides a bottom-up cross-sectional view of the cleaning system 700, and FIG. 8 provides a side perspective cross-sectional view of the cleaning system 700.

For example, cleaning system 700 includes a fan 710 which can be used to pull air (represented by arrow 760 of FIG. 8) from the cabin of the vehicle 100 into the cleaning system and through internal compartments 712, 714 of the cleaning system. The speed of the fan may be dependent upon the volume of air to be moved through the cleaning system for a given period of time and may be increased or decreased as needed or desired. Air then passes through an air cleaning device 720, 722. The air cleaning devices may include one or more various types of air cleaning features such as ionizers, ozonator, high pressure cleaning devices, or those that employ photochemical or photoelectrical oxidation, ultraviolet light sources for ultraviolet A (UVA), ultraviolet B (UVB) or UVC light rays, or any other devices which may be used for cleaning or sterilization of air, for example by killing viruses, bacteria, and fungi. The air may then exit the cleaning system 700 via one or more vents 730, 732, 734, 736 (represented by arrows 762, 764 of FIG. 8).

The air cleaning devices and fan may be run continuously, for instance whenever the vehicle 100 is running, in order to clean the air of the cabin whether or not the cabin is occupied.

The cleaning system may also include one or more surface cleaning devices for cleaning surfaces of the vehicle. For example, surface cleaning devices 740, 742, 744, 746 may be arranged within or proximate to each of the vents 730, 732, 734, 736 in order to enable rays from the surface cleaning device to escape the cleaning system and contact surfaces of the cabin of the vehicle, such as the seats 560, 570, 610, 620, 640, 650 and other surfaces of the cabin of vehicle 100. The surface cleaning devices may include one or more surface cleaning features such as devices for generating x-rays, RF or microwaves, gamma rays, as well as ultraviolet light sources for UVA, UVB or UVC light rays.

As noted above, the air and surface cleaning devices discussed herein may employ UVC light rays generated by UVC light sources to clean air and surfaces. As an example, UVC light may include radiation in the ultraviolet spectrum which extends from about 200 to 280 nm in wavelength. For example, different wavelengths, such as 222 nm, 256 nm and 273 nm, within the aforementioned range may provide different germicidal effectivity (e.g. being able to kill viruses, bacteria and fungi). In addition, the power and intensity of such devices as well as the amount of exposure time is critical to being able to kill viruses, bacteria and fungi. Larger pathogens such as fungi may require more power or intensity than bacteria, which may require more power or intensity than viruses. In addition, the greater the power, the lesser the exposure time required.

However, actual cleaning times for surfaces may be selected to be greater than necessary in order to ensure that viruses, bacterial and fungi receive a desired dosage of UVC light rays, or rather, one that is sufficient for such pathogens to be killed. For example, the surface cleaning may be on the order of 2 minutes or more or less. In addition, the surface cleaning may be continuous for this period of time (e.g. UVC light rays are generated until a desired dosage is achieved) or a high-power flash exposure (e.g. like a photographic flash) until the desired dosage is achieved. For a laser, rotation and/or well-known optical techniques of diffusers and beam shapers to distribute the light as well as flashing may be employed in order to cover the desired area with the desired dosage. In this regard, the faster the laser is rotated, the greater the dosage received by exposed surfaces of the cabin of the vehicle.

Examples of UVC light sources may include low pressure mercury ultraviolet tubes, UVC LED lights, or UVC lasers. Low pressure mercury ultraviolet tubes may provide relatively high-efficiency, with larger coverage areas and lower costs as compared to UVC LEDs though with less flexibility in form factor options. UVC LEDs may provide high flexibility in form factor options, but may have much lower efficiency and higher costs than Low pressure mercury ultraviolet tubes. UVC lasers may provide higher efficiency than other options, but may be more complex and have much higher costs than UVC LEDs and Low-pressure mercury ultraviolet tubes. The following table provides examples of different types of UVC light sources and their characteristics including germicidal effectivity for such characteristics.

TABLE

| UVC Light Sources and Germicidal Effectivity | | | | | | |
|---|---|---|---|---|---|---|
| UVC Light Source Type | Electrical Power | UVC Flux | Efficiency @ 254 nm | Ambient Temperature | Wavelength Peak (nm) | Germicidal effectivity |
| UVC - LED | | | ~1% | | 268 | ~95% |
| Low pressure mercury tube | 5-150 W | 0.1-0.5 W/cm | 25-40% | 40 deg C. | 254 (ozone free) | ~82% |
| Medium pressure mercury tube | 0.4-60 KW | 12-40 W/cm | ~15% | | 254 (ozone free) | ~82% |
| Amalgan UV | 50-80 W | 0.5-2 W/cm | ~35% | 90 deg C. | 254 (ozone free) | ~82% |
| Excimer UV | ~20 W | | | | 222 | ~82% |

The cleaning system 550 may also include sensors 750, 752, 754, 756 which can be used to detect whether the vehicle 100 is occupied by passengers or other occupants. As with sensors 530, 532, 534, 536 may include infrared sensors (to detect heat), passive infrared sensors (which can detect motion), inertial measurement units (IMUs) (which can be used to detect instances of passenger/luggage ingress to, egress from, the vehicle), load sensors on vehicle wheels/suspension (which can be used to detect loading of the vehicle for example, by comparing current weight to expected unladen vehicle weight—which may also include accounting for and fuel tank or cleaning fluids contents—against actual vehicle weight to detect presence of unaccounted mass in vehicle which can indicate occupancy, typical visible light cameras, event based cameras, stereo cameras (which may provide from three-dimensional information), time of flight cameras and/or an infrared cameras that can capture images of the vehicle in very low light conditions, such as at night time, during inclement weather, or when the vehicle is in a tunnel or parking garage.

Although not shown, the cleaning system 700 may include various other features including processing devices, connections and power sources. For example, in order to control the operation of the cleaning system 700, the cleaning system may include a communication connection in order to enable the computing devices 110 or other devices to communicate with the cleaning system 700, such as a CAN bus connection or ethernet connection. In this regard, the cleaning system 550 may be configured to control the speed of the fan 710 and/or activate the surface cleaning devices automatically upon receipt of a signal from the computing devices 110 and/or may include one or more computing devices configured similarly to computing devices 110 with processors and memory in order to enable the cleaning device to perform various functions described herein. The power source may include one or more batteries, such as rechargeable batteries, or other AC or DC power supply, such as a DC power supply from a battery of the vehicle 100.

The cleaning efficacy of UVC light rays may be hindered by surfaces within the vehicle. In other words, shaded areas of the vehicle which do not have a direct line of sight with the surface cleaning devices (such as the surface cleaning devices 740, 742, 744, 746) may not be sufficiently cleaned. To address this, various approaches may be used. For example, if the surfaces of the cabin, such as the seats 560, 570, 610, 620, 640, 650, dashboard area 510, headliner 540 and other surfaces of the cabin of vehicle 100, are highly reflective to UVC light rays, this may help to improve the percentages of surfaces that receive the desired dosage of UVC light rays.

Figure 9:
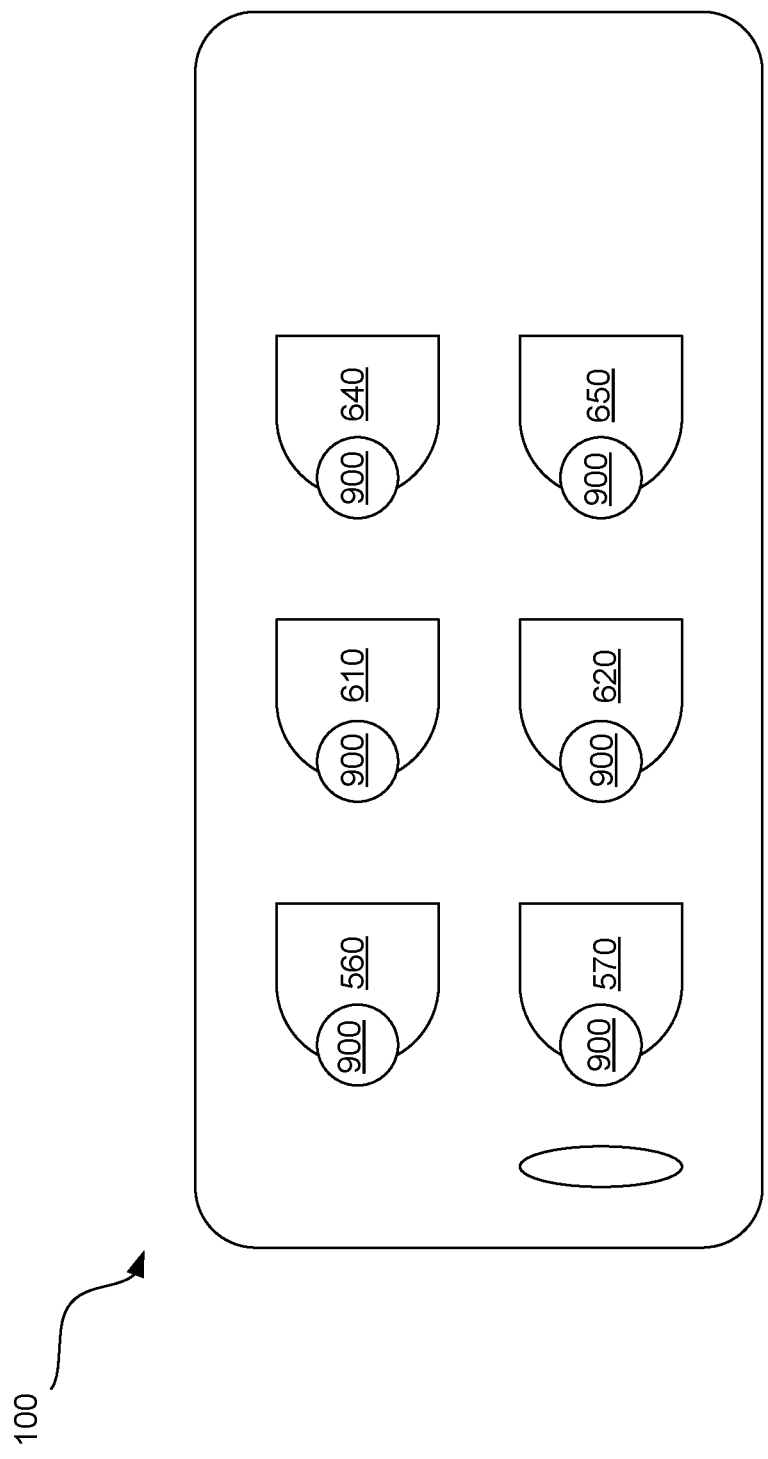
FIG. 9 is an example representation of a top-down view of a cabin of a vehicle in accordance with aspects of the disclosure.
Figure 10:
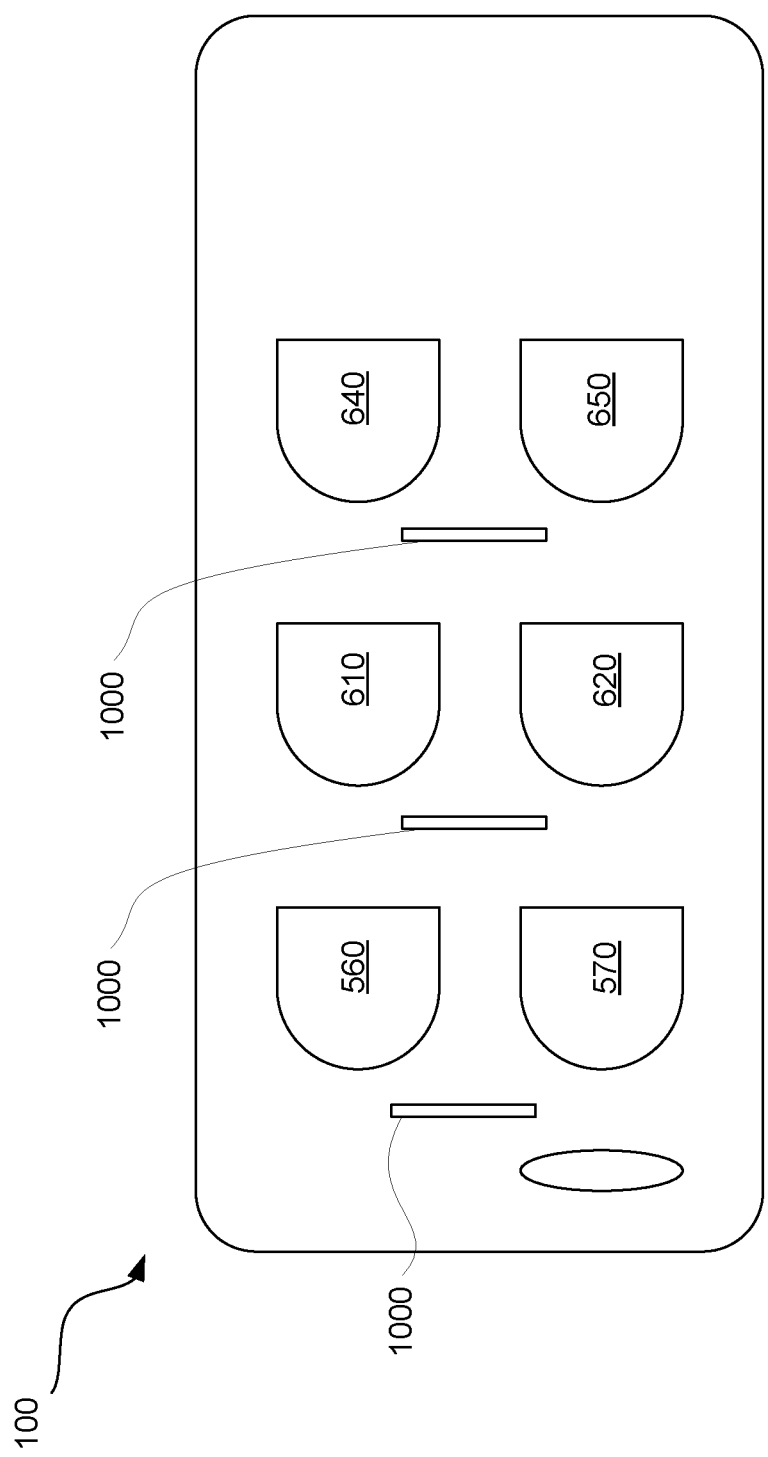
FIG. 10 is an example representation of a top-down view of a cabin of a vehicle in accordance with aspects of the disclosure.

In addition or alternatively, rather than employing a single cleaning device as shown in the example of cleaning system 550 depicted in FIG. 5, a plurality of cleaning devices may be arranged at different locations of the headliner 540. For example, turning to top-down views of example cabins of vehicle 100, FIGS. 9 and 10, a cleaning device may be located proximate to each of the seats of the vehicle 100. In the example of FIG. 9, each seat 560, 570, 610, 620, 640, 650 has its own cleaning system 900. As shown, there are six seats in the vehicle 100, and thus, there are six cleaning systems 900. In the example of FIG. 10, each row of seats has its own cleaning system 1000. As shown, there are three rows of seats in the vehicle 100, and thus, there are three cleaning systems 1000. The cleaning systems 900 and 1000 may be configured the same or similarly to the cleaning system 700, with air and surface cleaning devices, etc., though as shown, cleaning system 900 may be smaller in size than cleaning system 1000 for aesthetic and other reasons. For example, cleaning system 900 may be more compact while the cleaning system 1000 may be more elongated such that each respective cleaning device is able to move an appropriate amount of air proximate to a seat or row of seats as needed.

In addition or alternatively, rather than employing a stationary cleaning device as shown in the example of cleaning system 550 depicted in FIG. 5, a movable cleaning device may be arranged to move along a length of the headliner 540. For example, turning to top-down views of example cabins of vehicle 100, FIGS. 11 and 12, a cleaning system may be arranged to move along a path that enables the cleaning device to clean the surfaces of all of the seats of the vehicle 100.

Figure 11:
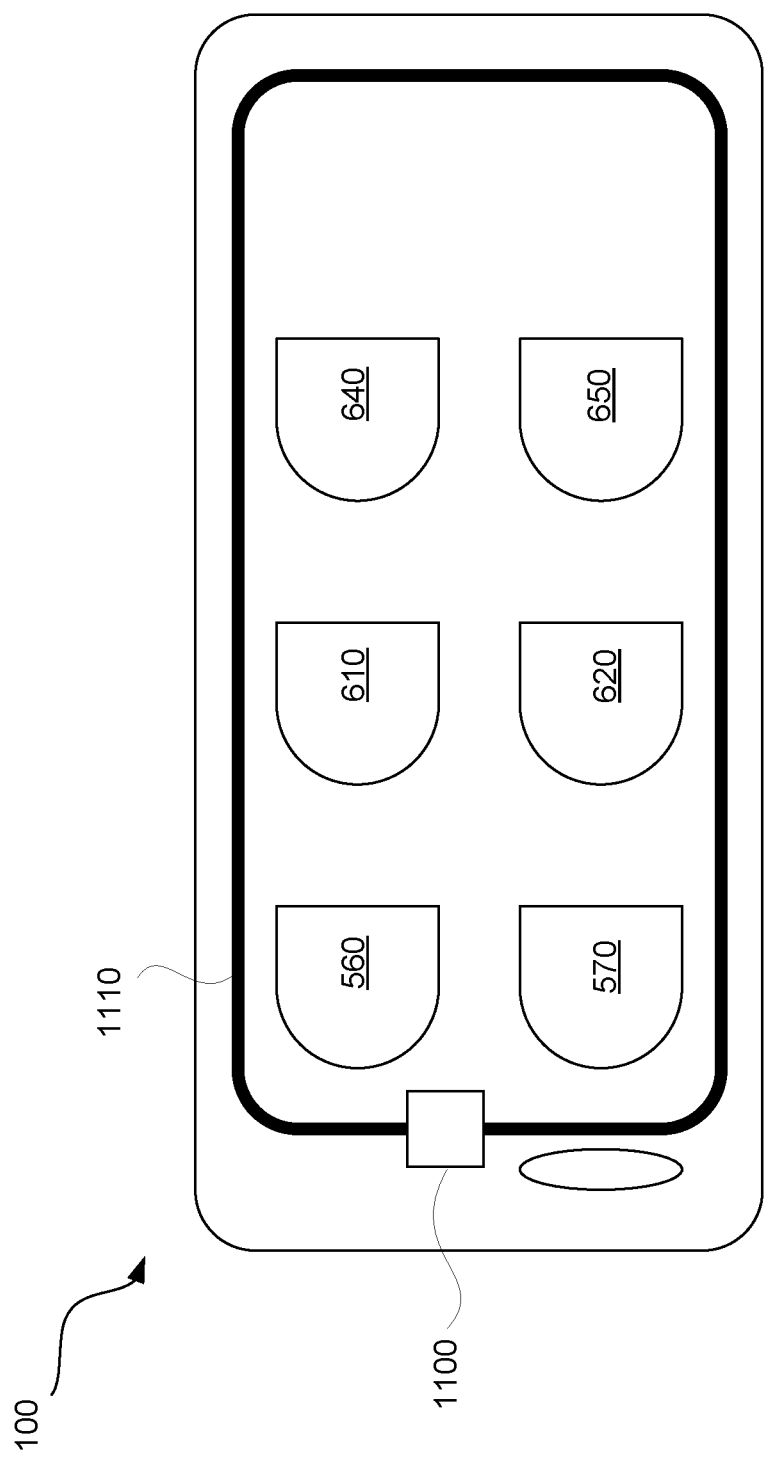
FIG. 11 is an example representation of a top-down view of a cabin of a vehicle in accordance with aspects of the disclosure.

In the example of FIG. 11, cleaning system 1100 is arranged on a single rail 1110 which may be attached to the headliner 540 (not shown). When activated, for instance by a signal from the computing devices 110, a motor (not shown) of the cleaning system 1100 may move the cleaning system along the rail 1110 in a loop around the interior of the vehicle. In some instances, a mechanical stub (or stop) may be arranged at some position on the rail 1110, such as in a rear corner of the vehicle to minimize the space or view interference to passengers or other occupants (such as a driver if there is one). The cleaning system 1100 may travel back and forth along the rail from one side of the stub to the other side of the stub. In such instances, the cleaning system may communicate with the computing devices 110 via a wireless connection such as Bluetooth. The cleaning system may stop at the stub, either through an infrared sensor or by using a force sensor to detect mechanical contact between the stub and the cleaning system. The cleaning system may be "parked" at the stub when the cleaning system (or at least the surface cleaning devices of the cleaning system) are not actively being used.

Figure 12:
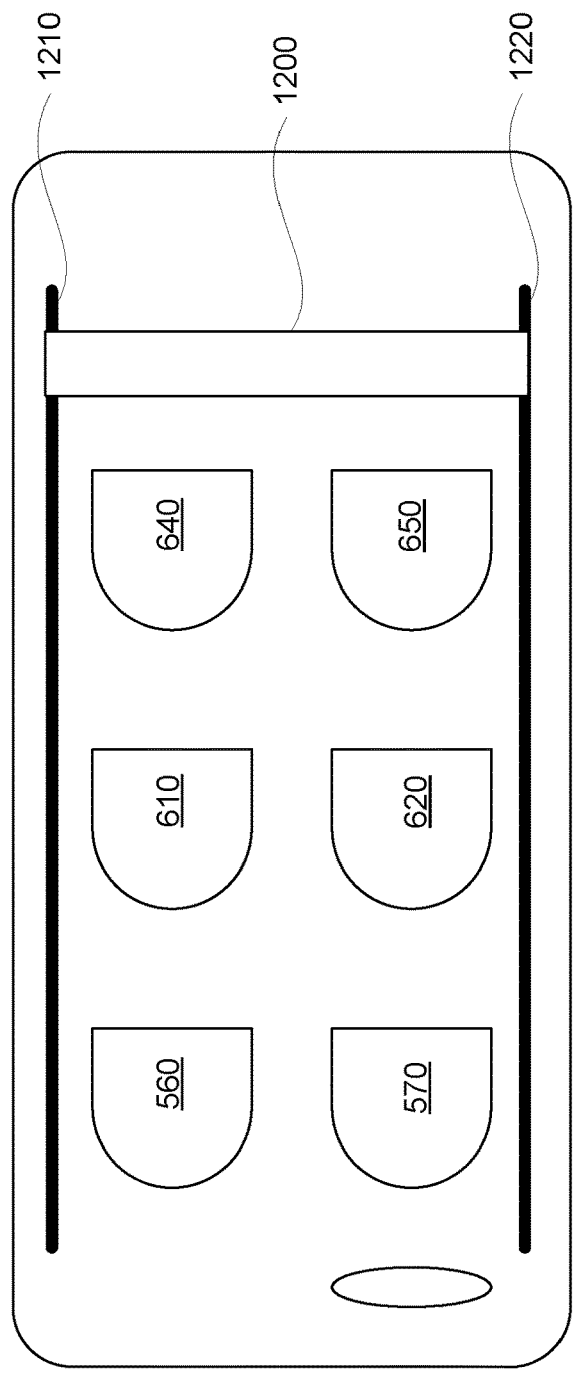
FIG. 12 is an example representation of a top-down view of a cabin of a vehicle in accordance with aspects of the disclosure.

In the example of FIG. 12, cleaning system 1200 is arranged on a pair of rails 1210, 1220 which may be attached to the headliner 540 (not shown). When activated, for instance by a signal from the computing devices 110, a motor (not shown) of the cleaning system 1200 may move the cleaning system along the rails 1210, 1220 in one direction towards the front of the vehicle and along the rails in another direction towards the rear of the vehicle. In some instances, a pair of mechanical stubs (or stop) may be arranged at the ends of each rail 1210, 1220 (e.g. two pairs or 4 stubs in total). The cleaning system 1200 may travel back and forth along the rails from one pair of stubs to the other. In such instances, the cleaning system 1200 may communicate with the computing devices 110 via a wireless connection such as Bluetooth. The cleaning system 1200 may stop at the stubs, either through an infrared sensor or by using a force sensor to detect mechanical contact between the stub and the cleaning system. The cleaning system 1200 may be "parked" adjacent to the pair of stubs at one end of the rails when the cleaning system (or at least the surface cleaning devices of the cleaning system) are not actively being used.

The cleaning systems 1100 and 1200 may be configured the same or similarly to the cleaning system 700, with air and surface cleaning devices, etc., though as shown, cleaning system 1100 may be shorter in length than cleaning system 1000 for aesthetic and other reasons, for example, to enable the cleaning device to attach to both rail 1210 and rail 1220.

Figure 13:
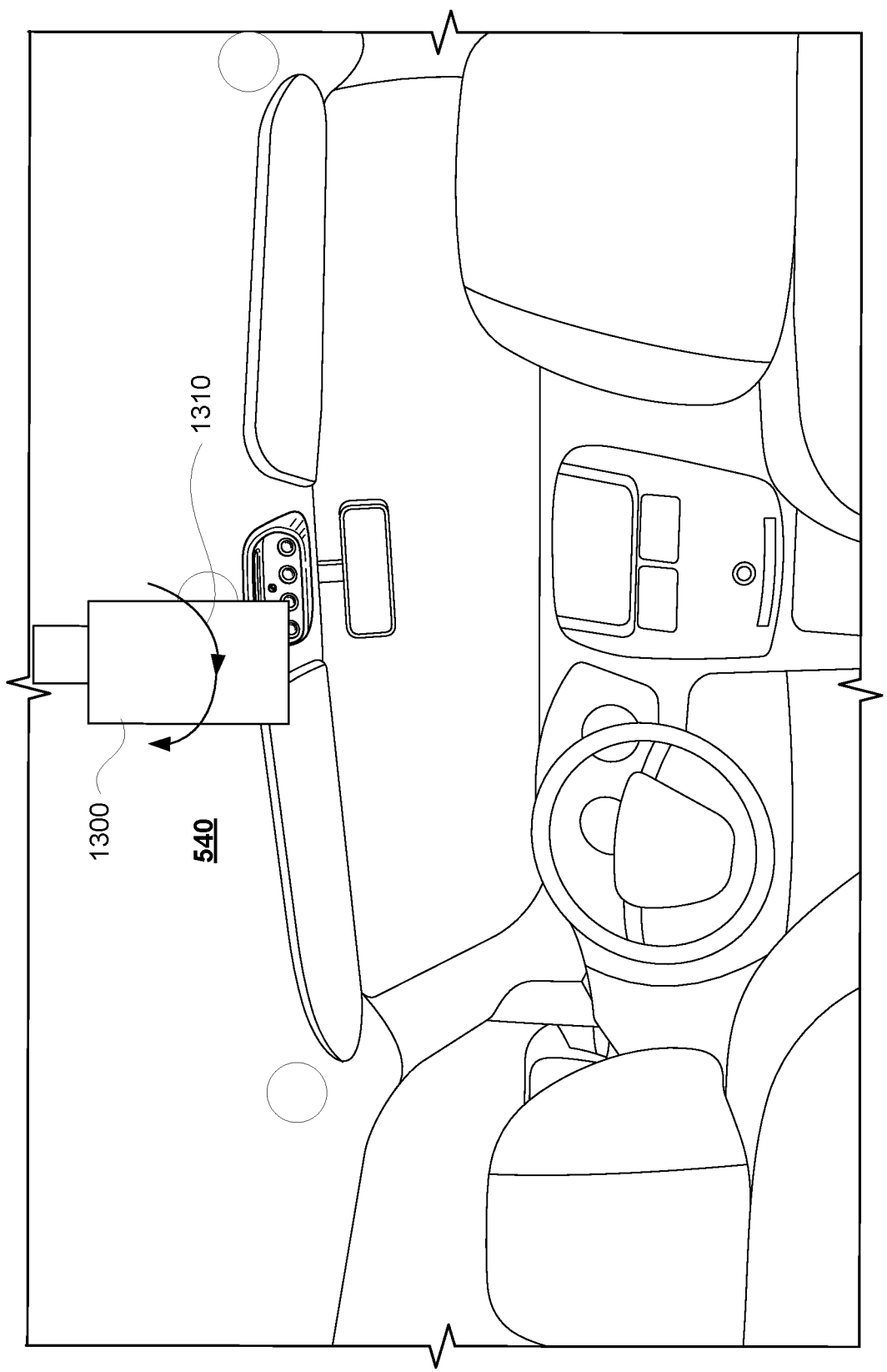
FIG. 13 is an example internal view of a cabin of a vehicle in accordance with aspects of the disclosure.

FIG. 13 provides another view of an example cabin of vehicle 100. In this example, cleaning system 1300 may be configured similarly to cleaning system 700, with air and surface cleaning devices, etc. However, at least the surface cleaning devices of the cleaning system 1300 may be configured to rotate, for example, in the direction of arrows 1310 or the opposite direction if desired. In this regard, cleaning system 1300 may include a surface cleaning device having a UVC laser. As noted above, rotation of the laser directly or beam steering using mirrors may be employed in order to cover the desired area with the desired dosage.

Figure 14:
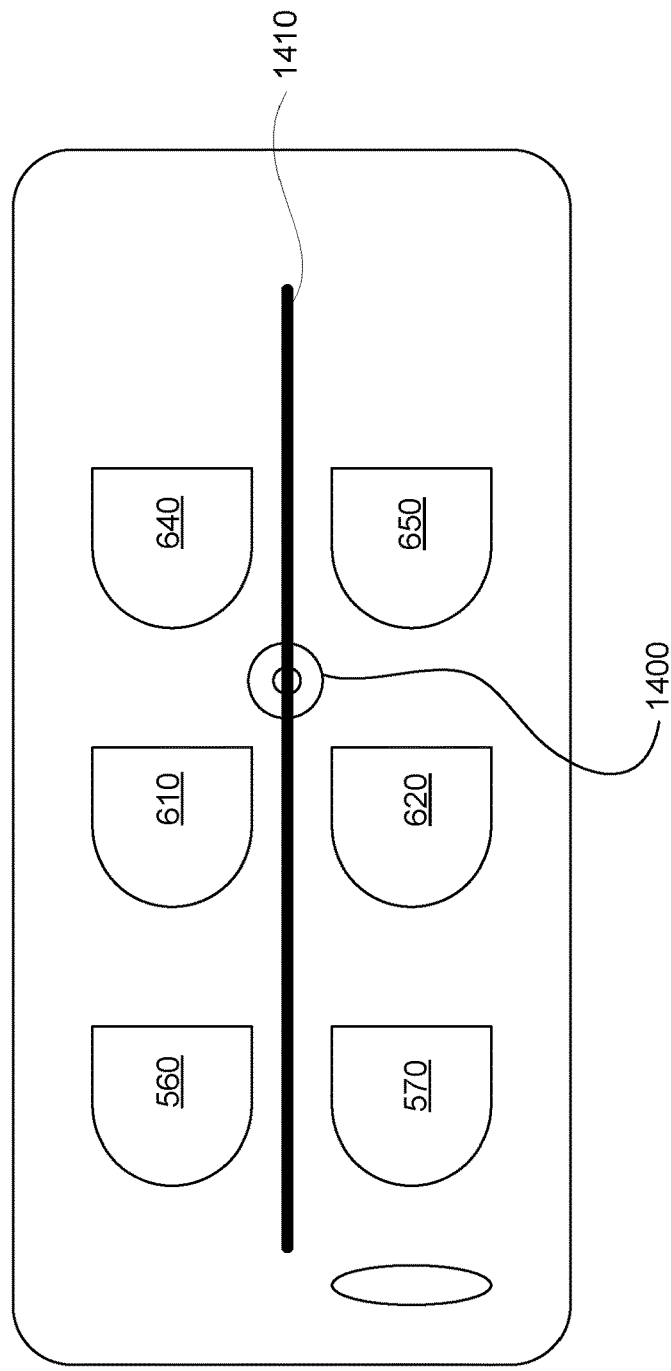
FIG. 14 is an example representation of a top-down view of a cabin of a vehicle in accordance with aspects of the disclosure.

In the example of FIG. 14, cleaning system 1400 is arranged on a single rail 1410 which may be attached to the headliner 540 (not shown). When activated, for instance by a signal from the computing devices 110, a motor (not shown) of the cleaning system 1400 may move the cleaning system along the rail 1410 in one direction towards the front of the vehicle and along the rail in another direction towards the rear of the vehicle. The cleaning system 1400 may be configured the same or similarly to the cleaning system 700, with air and surface cleaning devices, etc. However, as with cleaning system 1300, at least the surface cleaning devices of the cleaning system 1400 may be configured to rotate in one or more directions. In this regard, cleaning system 1400 may include a surface cleaning device having a UVC laser. As noted above, rotation of the laser directly or beam steering using mirrors may be employed in order to cover the desired area with the desired dosage.

In some instances, a mechanical stub (or stop) may be arranged at the ends of the rail 1410. The cleaning system 1400 may travel back and forth along the rails from one pair of stubs to the other. In such instances, the cleaning system may communicate with the computing devices 110 via a wireless connection such as Bluetooth. The cleaning system 1400 may stop at one of the stubs, either through an infrared sensor or by using a force sensor to detect mechanical contact between the stub and the cleaning system. The cleaning system 1400 may be "parked" adjacent to the stub at one end of the rail when the cleaning system (or at least the surface cleaning devices of the cleaning system) are not actively being used.

Alternatively, the cleaning systems described herein, including any of cleaning systems 550, 700, 900, 1000, 1100, 1200, 1300, 1400 may employ the aforementioned surface cleaning devices without also incorporating the fan and/or air cleaning devices. In such cases, the air cleaning devices may be integrated into an HVAC system of the vehicle. For example, a module including the features described above may be inserted into the HVAC system, for instance into a typical cabin filter replacement area, of vehicle 100 in order to provide air cleaning.

Figure 15:
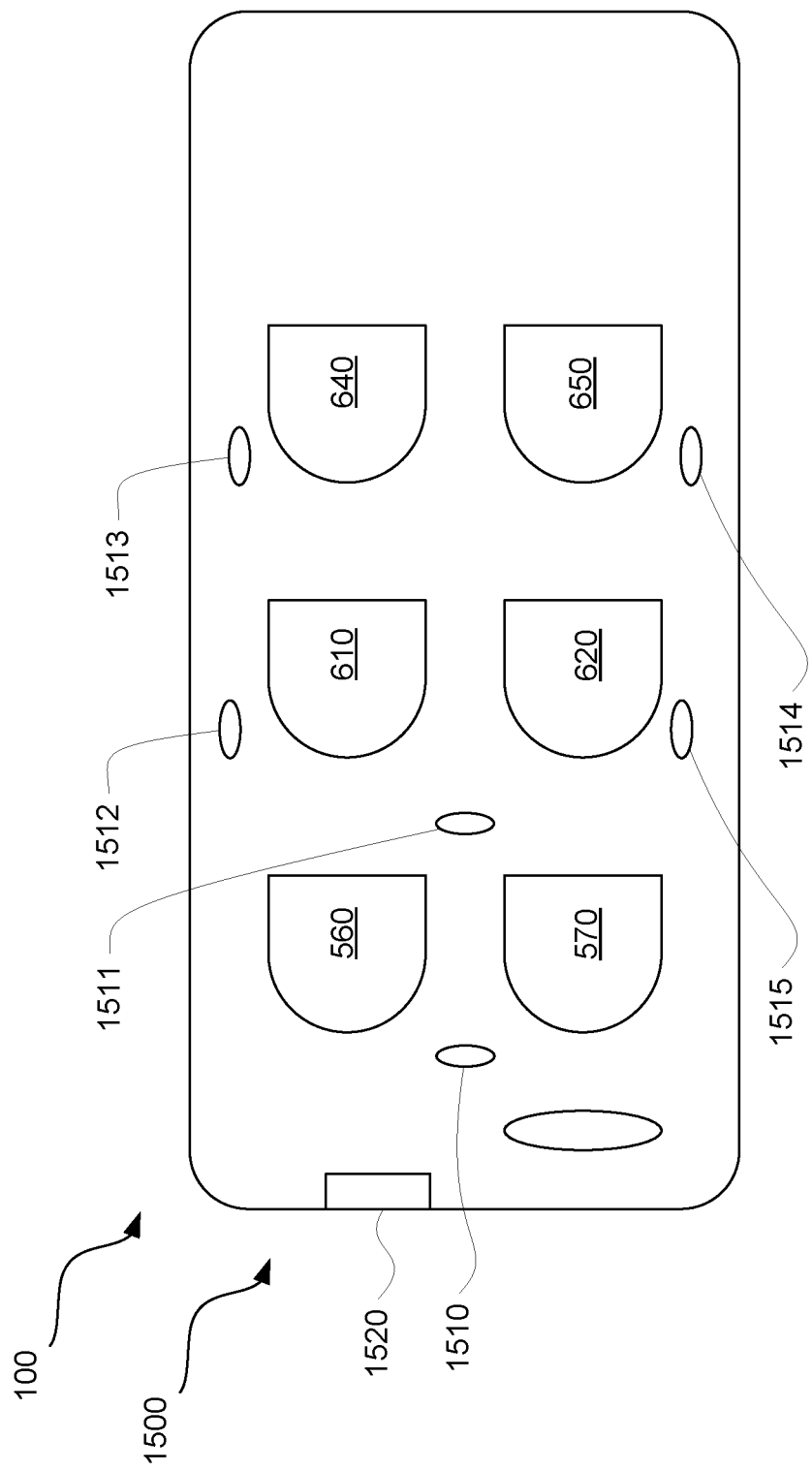
FIG. 15 is an example representation of a top-down view of a cabin of a vehicle in accordance with aspects of the disclosure.

FIG. 15 provides an example cleaning system 1500 which may include a plurality of surface cleaning devices 1510, 1511, 1512, 1513, 1514, 1515 arranged at different locations on or adjacent to the headliner 540 (not shown) or vehicle doors (such as doors 460, 462). In this example, the surface cleaning devices may have the same or a similar form factor as and be used to replace the typical cabin light modules in panels of the vehicle's doors, adjacent to the headliner, and in the headliner. This may enable the surface cleaning devices to utilize the electrical wiring and mechanical enclosures of the typical cabin light modules. The surface cleaning devices may be configured similarly to the surface cleaning devices 740, 742, 744, 746, and may utilize UVC light rays and/or other surface cleaning features as in the examples above. In addition, because these surface cleaning devices may replace typical cabin light modules, these surface cleaning devices may also include a typical light that can be activated by a passenger of the vehicle and/or the computing devices 110 as needed to illuminate the interior of the vehicle when passengers are present, ingressing or egressing, etc. These surface cleaning devices may be controlled by a centralized controller 1520 which may include other of the features of cleaning system 700, such as sensors, air cleaning devices, etc. Alternatively, as noted above, the air cleaning devices may be integrated into an HVAC system of the vehicle.

Example Methods

In addition to the operations described above and illustrated in the figures, various operations will now be described. It should be understood that the following operations do not have to be performed in the precise order described below. Rather, various steps can be handled in a different order or simultaneously, and steps may also be added or omitted.

As noted above, the cleaning systems 550, 700, 900, 1000, 1100, 1200, 1300, 1400, 1500 may employ UVC light rays to provide surface cleaning. While such light rays may be an effective way to kill viruses, bacteria and fungi, humans typically experience very little exposure. Most UVC light rays from the sun and other light sources do not penetrate the upper atmosphere. However, UVC light rays may cause damage to a person's skin or eyes, and may even cause diseases such as cancer or cataracts. In this regard, it may be critically important to ensure that the vehicle 100 is unoccupied by any passengers before utilizing the aforementioned surface cleaning devices. However, as noted above, the air cleaning devices may actually operate continuously, because if such devices utilize UVC light rays, they may be internal to the cleaning systems, and therefore may not raise concerns over exposure to passengers of the vehicle.

As noted above, these surface cleaning devices may employ UCV light sources in order to generate UVC light rays to provide for cleaning of surfaces within the vehicle. However, in order to avoid exposure of UVC light rays to passengers, the computing devices 110 may first attempt to confirm that the vehicle is unoccupied. As such, the surface cleaning may be scheduled to be activated between passenger rides or during rides which do not include any passengers, such as those that transport only cargo. In this regard, the surface cleaning may be utilized fairly often without impacting availability of the service. In some instances, when scheduling between rides, once the vehicle 100 reaches a drop off location for a passenger, the computing devices 110 may initiate an end of trip check to confirm that the vehicle is unoccupied.

Figure 16:
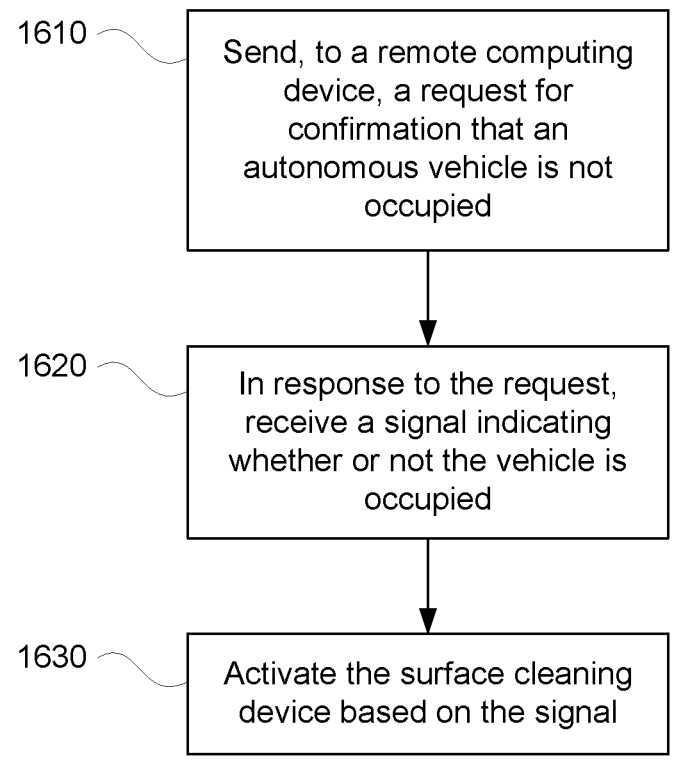
FIG. 16 is an example flow diagram in accordance with aspects of the disclosure.

The end of trip check may include confirming that the vehicle is empty and activating the surface cleaning devices. FIG. 16 is an example flow diagram 1600 in accordance with aspects of the disclosure which may be performed by one or more processors of one or more computing devices, such as processors 120 of computing devices 110, in order to clean interior surfaces of a vehicle, such as vehicle 100. For example, turning to block 1610, a request for confirmation that the vehicle is not occupied is sent. For instance, this may involve sending feedback or signals from the one or more sensors 530, 532, 534, 536, 750, 752, 754, 756 to a remote computing device via a network, such as network 260. In addition, the computing devices 110 may send feedback or signals from other types of sensors, such as those used to determine the status of a door (e.g. open or closed), pressure sensors used to determine whether a person is sitting in a seat of the vehicle, etc. In addition, in the examples of cleaning systems 1100, 1200, 1300, 1400 these cleaning systems may be moved along the rails and/or rotated, respectively, to allow any sensors to capture feedback or signals which may be sent to the remote computing device as well.

The remote computing device may be a concierge workstation, such as concierge work station 240, manned by a human operator, such as concierge 242. The concierge work station 240 may display the feedback or signals from the one or more sensors 530, 532, 534, 536, 750, 752, 754, 756 or other types of sensors, for example, on display 244. As an example, the concierge may review still or video images from the sensors and may use this information to determine whether the vehicle 100 is occupied by passengers or other persons. The concierge may identify whether or not the vehicle is occupied (i.e. yes or no), for example, using the user inputs 246 of the concierge work station 240. The concierge work station 240 may then send a signal identifying whether or not the vehicle is occupied back to the computing devices 110, for example, via network 260.

At block 1620 of FIG. 16, in response to the request, a signal identifying whether or not the vehicle is occupied may be received. The signal may explicitly include this information or may indicate other information, such as that the vehicle should or may use surface cleaning devices. In this regard, in response to the request, the computing devices 110 may receive the signal. Based on the signal, the computing devices 110 may determine whether to activate the surface cleaning devices 740, 742, 744, 746, 1510, 1511, 1512, 1513, 1514, 1515. For instance, when the signal indicates that the vehicle is occupied, the computing devices 110 would not activate the surface cleaning devices in order to prevent any exposure to any passengers or other persons, for example, to UVC light rays.

At block 1630 of FIG. 16, the surface cleaning devices may be activated based on the received signal. When the signal indicates that the vehicle is not occupied, the computing devices 110 may send a signal to a cleaning device, such as cleaning systems 550, 700, 900, 1000, 1100, 1200, 1300, 1400, 1500 in order to activate the aforementioned surface cleaning devices 740, 742, 744, 746, 1510, 1511, 1512, 1513, 1514, 1515. In the examples of cleaning systems 1100, 1200, 1300, 1400, this may involve causing the cleaning devices to move along the rails 1110, 1210, 1220, 1410 towards the front and/or rear of the vehicle and/or be rotated (as in the case of cleaning systems 1300, 1400). As noted above, the surface cleaning devices may provide a desired amount of exposure to the cabin of the vehicle, including surfaces of such as the seats 560, 570, 610, 620, 640, 650, dashboard area 510 (including the steering wheel), headliner 540, door handles, and other surfaces of the cabin of vehicle 100.

The computing devices 110 may send the request and activate the surface cleaning devices (when appropriate) while the vehicle is stationary or moving. For instance, rather than waiting for the cleaning to be complete before moving to the next destination (e.g. to pick up a new passenger), the request and/or activation of the surface cleaning devices may be performed while the vehicle is on its way to the vehicle's next destination. In this regard, the cleaning of surfaces of the interior of the vehicle may have very little impact on the transportation service.

In addition, by utilizing a human operator to review feedback and signals from various sensors, rather than relying only on the computing devices 110, a human operator is able to check and confirm remotely that the vehicle is not occupied before activating the surface cleaning devices, thus greatly decreasing the likelihood of accidental exposure of passengers or other persons to UVC light rays. In addition, in some cases, the human operator may be better able to identify a partially occluded object as a person than the computing devices 110, thus improving the safety of the system. For instance, a concierge might be able to better recognize a portion of a person who is hiding behind a seat and thus may determine that the vehicle is occupied, even where the computing devices 110 would not make the same determination.

In addition or alternatively, the computing devices 110 may also determine whether the vehicle is occupied or not occupied. For example, the computing devices may receive feedback or signals from one or more of sensors 530, 532, 534, 536, 750, 752, 754, 756, in order to determine whether the vehicle is occupied. In addition, the computing devices 110 may receive feedback or signals from the other types of sensors, such as those used to determine the status of a door, pressure sensors used to determine whether a person is sitting in a seat of the vehicle, etc. as described above. In addition, in the examples of cleaning systems 1100, 1200, 1300, these cleaning systems may be moved along the rails or rotated, respectively, to allow any sensors to capture feedback or signals which may be used by the computing devices 110 as well. The more signals that are used in multiple locations (including on the cleaning devices or surfaces of the vehicle), the more likely that the determination of whether a vehicle is occupied or unoccupied will be accurate.

Using feedback or signals from the various sensors, the computing devices 110 may determine whether the vehicle is occupied (or not occupied) by a passenger or other person using known approaches for doing so based on the various feedback and signals received. At the same time, the computing devices 110 may estimate a confidence (e.g. a numerical value) in this determination based on the reliability of each of the sensors at detecting whether the vehicle is occupied or unoccupied, the number of signals that suggest that the vehicle is occupied or unoccupied, etc.

If the computing devices 110 determine that the vehicle is occupied with a particular confidence, the computing devices 110 would not activate the surface cleaning devices. In other words, if there is at least some threshold possibility of the vehicle being occupied, such occupants would not be exposed to UVC light rays from the surface cleaning devices. The method of calculation of confidence level and determination of thresholds can be made with supervised machine learning techniques. A confidence level that has extremely high recall against training data could initiate automatic cleaning without confirmation from a concierge. A lower confidence level would require confirmation, and perhaps an even lower confidence level would not even bother to request human confirmation in order to not overload the concierges.

Alternatively, if the computing devices determine that the vehicle is unoccupied with a high confidence, for example, a confidence that meets a threshold value such as 99% or higher, the computing devices 110 may automatically activate the surface cleaning devices. In such cases, if the computing devices 110 determine that the vehicle is unoccupied with a confidence that does not meet the threshold value, the computing devices 110 may automatically send the aforementioned request for confirmation that the vehicle is currently empty to a remote computing device as described above. In this regard, the concierge may function as a backstop to again ensure that the vehicle is unoccupied before the surface cleaning devices are activated.

As another alternative, the computing devices 110 may always make an initial determination of whether a vehicle is occupied or not, but may send this determination and the confidence to the remote computing device as part of the request for confirmation that the vehicle is not occupied. In this regard, a concierge reviewing the feedback or signals from the sensors may have an additional data point to help the concierge make a more informed decision.

As yet another alternative, in response to receiving the signal from the remote computing device, the computing devices 110 may run a further analysis to determine whether the vehicle is unoccupied. In this regard, even where a concierge finds that a vehicle is unoccupied, if the computing devices 110 thereafter determine that the vehicle is occupied, the computing devices may "override" the determination of the concierge.

In addition, during the surface cleaning, the computing devices 110 may continue to use the feedback or signals from the sensors 530, 532, 534, 536, 750, 752, 754, 756 (and/or the aforementioned other sensors) to confirm that the vehicle is not occupied. If the computing devices 110 determine that the vehicle is occupied, the computing devices may automatically send a signal to the cleaning systems to deactivate the surface cleaning devices. This may further reduce the likelihood of exposure of passengers or other occupants to the UVC light rays. In the examples of cleaning systems 1100, 1200, 1300, as these cleaning systems move along their respective rails or rotate, the computing devices 110 may use the sensors on these cleaning devices to continuously look for passengers or other occupants.

In addition, in the unlikely event that the vehicle was occupied and the surface cleaning devices are activated, any cleaning systems may have an emergency stop button that can be easily reached by an occupant in order to deactivate any surface cleaning devices. The emergency stop button may be a dedicated physical button, or it may be displayed on the internal electronic display 152 prior to initiation of cleaning, or the client computing device 220, 230, or any combination thereof.

Vehicle windows may be opaque to UVC light rays which may prevent exposure of any persons outside of the vehicle 100 to the UVC light rays. Thus it may be important to also confirm that the vehicle's windows, such as windows 464, 464, and doors, such as doors 460, 462, are closed before activating the surface cleaning devices. For example, the computing devices 110 may send a signal to a controller for automatically opening and closing windows of the vehicle prior to activating the surface cleaning devices and wait an appropriate amount of time before activating the surface cleaning devices. Similarly, the computing devices 110 may send a signal to a controller for automatically opening and closing doors of the vehicle prior to activating the surface cleaning devices and wait an appropriate amount of time before activating the surface cleaning devices. In addition or alternatively, a human operator, such as the concierge discussed above, may use the feedback and signals from the sensors to further confirm that the vehicle's windows and doors are closed.

In addition or alternatively, the computing devices 110 may use information from the perception system 172 to check the perimeter around the vehicle to confirm that there are no people around the vehicle in order to further reduce the likelihood of exposure of any persons outside of the vehicle 100 to the UVC light rays.

The surface cleaning described herein may be done at various intervals. For example, the surface cleaning devices may be activated between all rides, after so many rides (e.g. every third trip, etc.), between only certain types of rides (e.g. those with multiple riders, etc.), or once or twice per day. For example, it may make sense to utilize the surface cleaning devices more often depending on season (e.g. more often during flu season than during summer months). As another example, an external infrared camera or other thermal imaging device may be used to check the temperatures of passengers to be picked up for a trip, and if elevated, the surface cleaning devices may be activated immediately after the trip. As another example, external and/or internal microphones may be used to detect whether a potential or current passenger for a trip is coughing. In such cases, the surface cleaning devices may be activated immediately after the trip.

As another example, the surface cleaning devices may be utilized for certain types of passengers, such as rides including younger or older passengers, those who are more vulnerable or at risk (e.g. compromised immune systems or underlying health conditions), or those who specifically pay for cleaning as part of their trip. In this regard, when a vehicle is dispatched to pick up such passengers by the server computing devices 210, the dispatching instructions may include instructions to activate the surface cleaning devices. In such instances, the computing devices 110 may then attempt to determine whether the vehicle is occupied as described in any of the examples above.

The features described herein may provide a useful and reliable way to clean the interior of a vehicle. As noted above, in addition to cleaning the air of the cabin of a vehicle, the cleaning systems and devices described herein may provide a safe and reliable way to clean surfaces of a vehicle. In addition, by utilizing UVC light rays, the cleaning may attempt to sanitize or disinfect surfaces of the vehicle by killing viruses, bacteria and fungi. UVC light rays may be utilized more often with autonomous vehicles which do not require a driver as compared to typical taxies with a human driver because there may be more opportunities to clean the vehicle (i.e. times when there are no occupants within the vehicle) between passenger rides or during rides without any passengers (or driver) to transport cargo. In addition, by utilizing a human operator to review feedback and signals from various sensors, rather than relying only on the computing devices of the vehicle, a human operator is able to check and confirm remotely that the vehicle is not occupied before activating the surface cleaning devices, thus greatly decreasing the likelihood of accidental exposure of passengers or other persons to UVC light rays. In addition, in some cases, the human operator may be better able to identify a partially occluded object as a person than the computing devices of the vehicle, thus improving the safety of the cleaning systems as well as the vehicle. Moreover, by utilizing the surface cleaning devices between rides, the cleaning need not impact the availability of a transportation service.

In addition, in transportation services operated by a human driver, vehicle interior cleaning cannot not eliminate the risk of contamination from illness carried by the driver, thus the utility of deep cleaning is diminished. Conversely, in a transportation service with fully autonomous vehicles, passengers may be attracted to a service because it may be capable of offering higher levels of cleanliness and isolation from contaminants. So passengers with such concerns may place a premium on the cleaning afforded by the features described herein. Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements.

The invention claimed is:

1. A method for activating surface cleaning to clean interior surfaces of an autonomous vehicle, the method comprising:
    sending, by one or more processors of the vehicle to a remote computing device, a request for confirmation that the vehicle is not occupied;
    in response to the request, receiving, by the one or more processors from the remote computing device, a signal indicating that a human operator has determined that the vehicle is not occupied; and
    activating, by the one or more processors, a surface cleaning device based on the received signal.

2. The method of claim 1, wherein the surface cleaning device includes a UVC light source in order to clean the interior surfaces.

3. The method of claim 1, wherein the sending further includes sending feedback from one or more sensors mounted within the vehicle.

4. The method of claim 3, wherein the surface cleaning device is incorporated into a cleaning system including the one or more sensors.

5. The method of claim 1, further comprising, determining, by the one or more processors, based on feedback from one or more sensors, whether the vehicle is occupied, and wherein the sending is after the determining.

6. The method of claim 5, wherein the sending further includes sending the determination of whether the vehicle is occupied to the remote computing device.

7. The method of claim 6, further comprising
determining a confidence for the determination of whether the vehicle is occupied; and
determining whether the confidence meets a threshold value, and wherein the sending is based on the determining whether the confidence meets the threshold value.

8. The method of claim 1, wherein the sending is performed between rides for the vehicle, wherein each of the rides includes the vehicle transporting passengers or cargo.

9. The method of claim 8, wherein the activating is performed while the vehicle is moving between the rides.

10. The method of claim 8, wherein the activating is performed while the vehicle is stationary between the rides.

11. The method of claim 1, wherein the sending is in response to receiving dispatching instructions to pick up a passenger.

12. The method of claim 11, wherein the dispatching instructions include a request for the vehicle to activate the surface cleaning device.

13. The method of claim 1, wherein the activating includes sending a signal to a cleaning system to cause the surface cleaning device to move along one or more rails within the vehicle.

14. The method of claim 1, further comprising, after activating the surface cleaning device and while the surface cleaning device is activated, determining, by the one or more processors, based on feedback from one or more sensors, whether the vehicle is occupied.

15. The method of claim 14, wherein when the vehicle is determined to be occupied, deactivating the surface cleaning device.

16. The method of claim 1, further comprising, prior to activating the surface cleaning device, confirming, by the one or more processors, that windows of the vehicle are closed.

17. The method of claim 1, further comprising, prior to the activating, using information from a perception system of the vehicle including one or more sensors to check an area around the vehicle for people.

18. A system for activating surface cleaning to clean interior surfaces of an autonomous vehicle, the system comprising:
a surface cleaning device including a UVC light source; and
one or more processors configured to:
send, to a remote computing device, a request for confirmation that the vehicle is not occupied,
in response to the request, receive, from the remote computing device, a signal indicating that a human operator has determined that the vehicle is not occupied, and
activate a surface cleaning device based on the received signal.

19. The system of claim 18, further comprising the vehicle.

* * * * *